US006495544B2

(12) United States Patent
Hansen, Jr. et al.

(10) Patent No.: US 6,495,544 B2
(45) Date of Patent: Dec. 17, 2002

(54) HOMOIMINOPIPERIDINYL HEXANOIC ACID INHIBITORS OF INDUCIBLE NITRIC OXIDE SYNTHASE

(75) Inventors: Donald W. Hansen, Jr., Skokie, IL (US); Jeffrey S. Snyder, Manchester; Alan E. Moormann, Weldon Springs, both of MO (US); Alok K. Awasthi, Skokie, IL (US); Ronald Keith Webber, St. Charles; Thaddeus S. Franczyk, Chesterfield, both of MO (US); Mahima Trivedi, Skokie, IL (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/920,612

(22) Filed: Aug. 1, 2001

(65) Prior Publication Data

US 2002/0119964 A1 Aug. 29, 2002

Related U.S. Application Data

(60) Provisional application No. 60/222,179, filed on Aug. 1, 2000.

(51) Int. Cl.$^7$ .................. A61K 31/55; C07D 223/10; C07D 267/02; C07D 223/08; C07D 223/12
(52) U.S. Cl. .................. 514/217.11; 540/531; 540/552; 540/604; 540/605
(58) Field of Search .................. 540/531, 552, 540/604, 605; 514/217.11

(56) References Cited

U.S. PATENT DOCUMENTS

| 5,854,234 A | 12/1998 | Hansen et al. ............. 514/212 |
| 5,994,391 A | 11/1999 | Lee et al. .................. 514/431 |

FOREIGN PATENT DOCUMENTS

| EP | 0521471 B1 | 1/1993 | ......... C07D/239/38 |
| WO | WO9511231 | 4/1995 | ......... C07D/207/22 |
| WO | WO9633175 | 10/1996 | ......... C07D/223/22 |
| WO | WO9706802 | 2/1997 | ......... A61K/31/495 |
| WO | WO9964426 | 12/1999 | ......... C07D/498/04 |

OTHER PUBLICATIONS

S Moncada and EA Higgs, *FASEB Journal*, 9: 1319–1330 1995.
WO 99/64426 (Abstract).*

* cited by examiner

*Primary Examiner*—Bruck Kifle
(74) *Attorney, Agent, or Firm*—Philip B. Polster, II

(57) ABSTRACT

Homoiminopiperidinyl Hexanoic Acid derivatives and pharmaceutically acceptable salts thereof useful in the inhibition of the inducible isoform of nitric oxide synthase are disclosed.

27 Claims, No Drawings

HOMOIMINOPIPERIDINYL HEXANOIC ACID INHIBITORS OF INDUCIBLE NITRIC OXIDE SYNTHASE

CROSS REFERENCE TO RELATED APPLICATIONS

This application claims the benefit of U.S. Provisional Application Serial No. 60/222,179, filed Aug. 1, 2000.

FIELD OF THE INVENTION

The present invention relates to homoiminopiperidinyl hexanoic acid derivatives and their use in therapy, in particular their use as nitric oxide synthase inhibitors.

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed, this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase, such consequences including hypertension and possible thrombosis and tissue damage. In particular, in the case of the therapeutic use of L-NMMA (a non-selective NO synthase inhibitor) for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

U.S. Pat. No. 5,854,234, the disclosure of which is hereby incorporated by reference in its entirety as if written herein, discloses compounds that inhibit nitric oxide synthesis and preferentially inhibit the inducible isoform of nitric oxide synthase.

SUMMARY OF THE INVENTION

Compounds have now been found which are highly selective inhibitors of Inducible Nitric Oxide Synthase (iNOS).

In a broad aspect, the present invention is directed to novel compounds, pharmaceutical compositions, process for preparing novel compounds, process for preparing pharmaceutical compositions, and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

Compounds of the present invention will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID, opioid analgesic or certain anticonvulsants would traditionally be administered.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temperoramandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive. heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2

("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PLAC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid).

A further embodiment provides a therapeutic combination of a compound of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-la$^2$, glu$^4$]deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

DETAILED DESCRIPTION OF THE INVENTION

In its broadest sense, the invention is represented by the compounds of formula

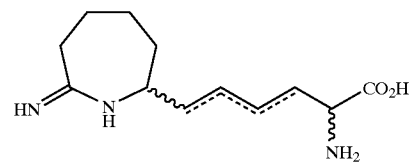

In another embodiment, the invention is represented by the compound

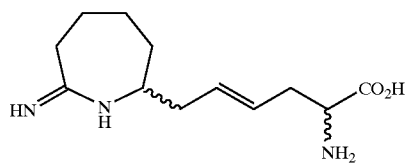

In another embodiment, the invention is represented by the compound

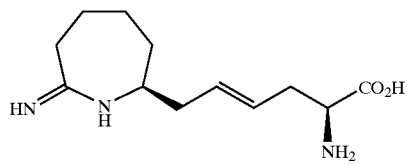

In another embodiment, the invention is represented by the compound

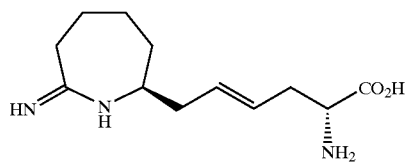

In another embodiment, the invention is represented by the compound

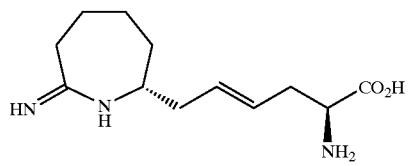

In another embodiment, the invention is represented by the compound

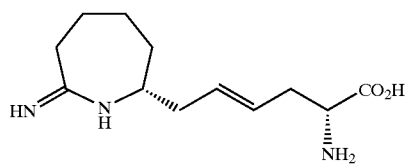

In another embodiment, the invention is represented by the compound

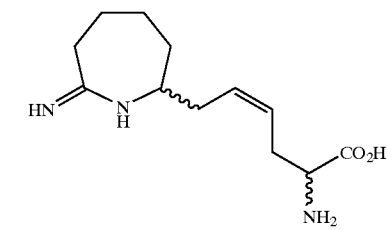

In another embodiment, the invention is represented by the compound

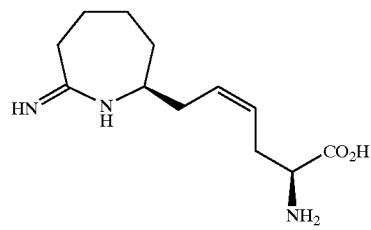

In another embodiment, the invention is represented by the compound

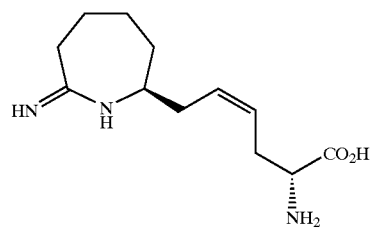

In another embodiment, the invention is represented by the compound

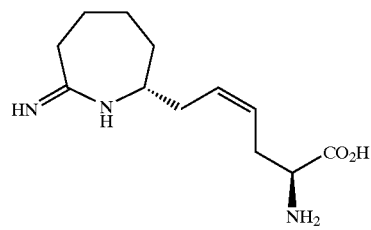

In another embodiment, the invention is represented by the compound

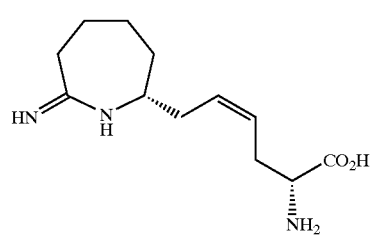

In a further embodiment of the present invention, the compound is represented by the formula:

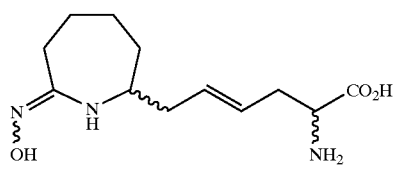

Still another embodiment is represented by the compound:

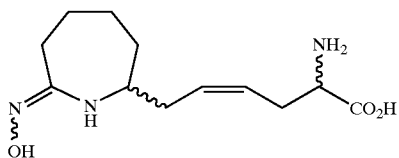

In another embodiment, the invention is represented by the compound:

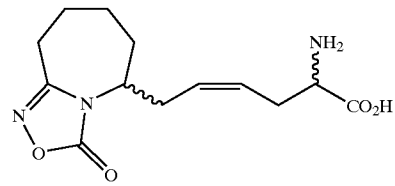

Still another embodiment is represented by the compound:

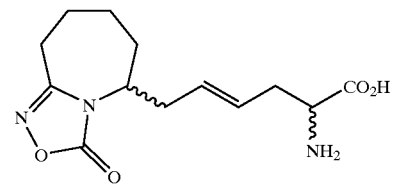

In another embodiment, the invention is represented by the compound:

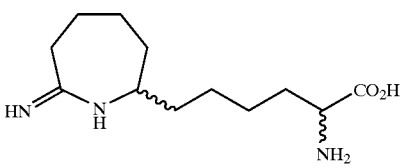

In another embodiment, the invention is represented by the compound

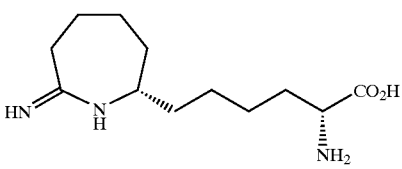

Still another embodiment is represented by the compound

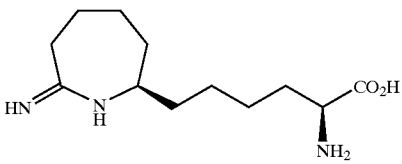

And a further embodiment is represented by the compound

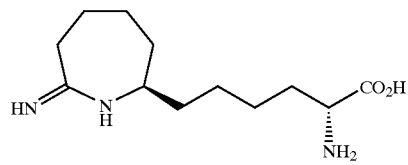

Another embodiment is further represented by the compound

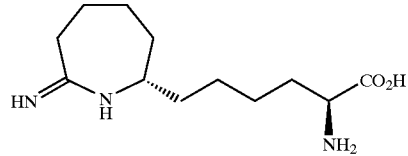

Also included in the family of the above compounds are the pharmaceutically-acceptable salts thereof. The term "pharmaceutically-acceptable salts" embraces salts commonly used to form alkali metal salts, alkaline earth metal salts and to form addition salts of free acids or free bases. The nature of the salt is not critical, provided that it is pharmaceutically acceptable. Suitable pharmaceutically-acceptable acid addition salts of compounds of Formula I may be prepared from inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. All of these salts may be prepared by conventional means from the corresponding compounds by reacting, for example, the appropriate acid or base with the compound. As examples, and not intended to limit the invention to any particular salt, the following salt forms of the invention are included:

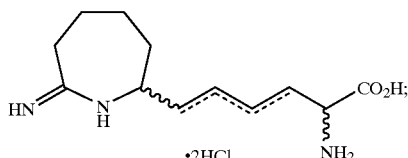

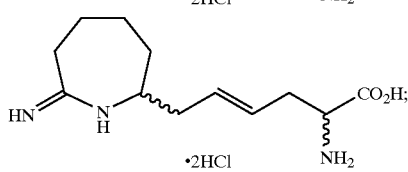

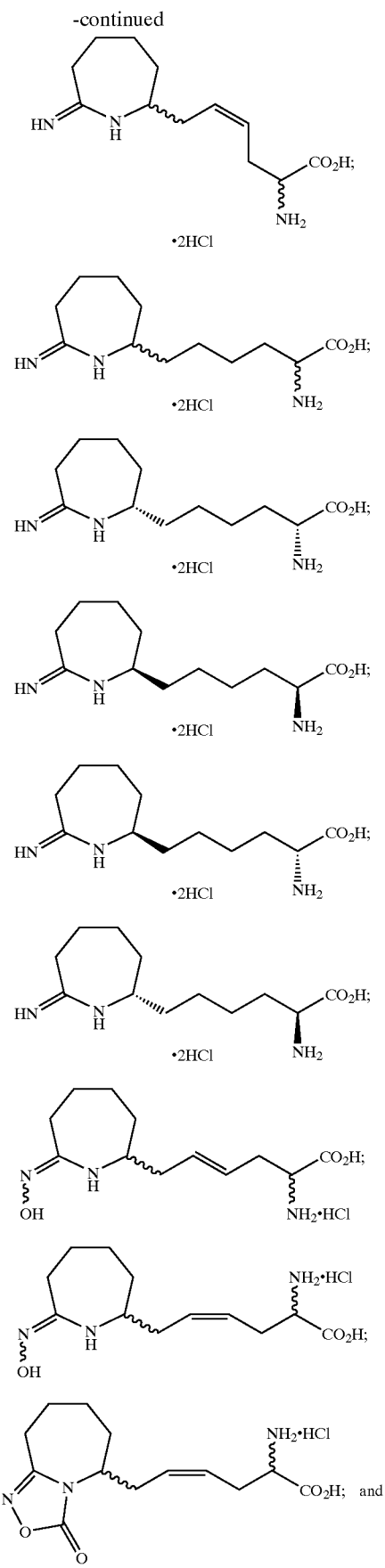

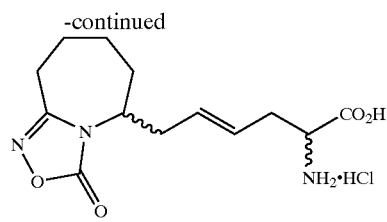

While it may be possible for the compounds to be administered as the raw chemical, it is preferable to present them as a pharmaceutical composition. According to a further aspect, the present invention provides a pharmaceutical composition comprising the compound or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound or a pharmaceutically acceptable salt or solvate thereof with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 0.5 mg to 200 mg, usually around 0.5 mg to 100 mg.

The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric or stereoisomeric forms. The present invention contemplates all such compounds, including R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention.

Some of the compounds described contain one or more stereocenters and are meant to include R, S, and mixtures of R and S forms for each stereocenter present.

The following schemes are useful in making the present invention.

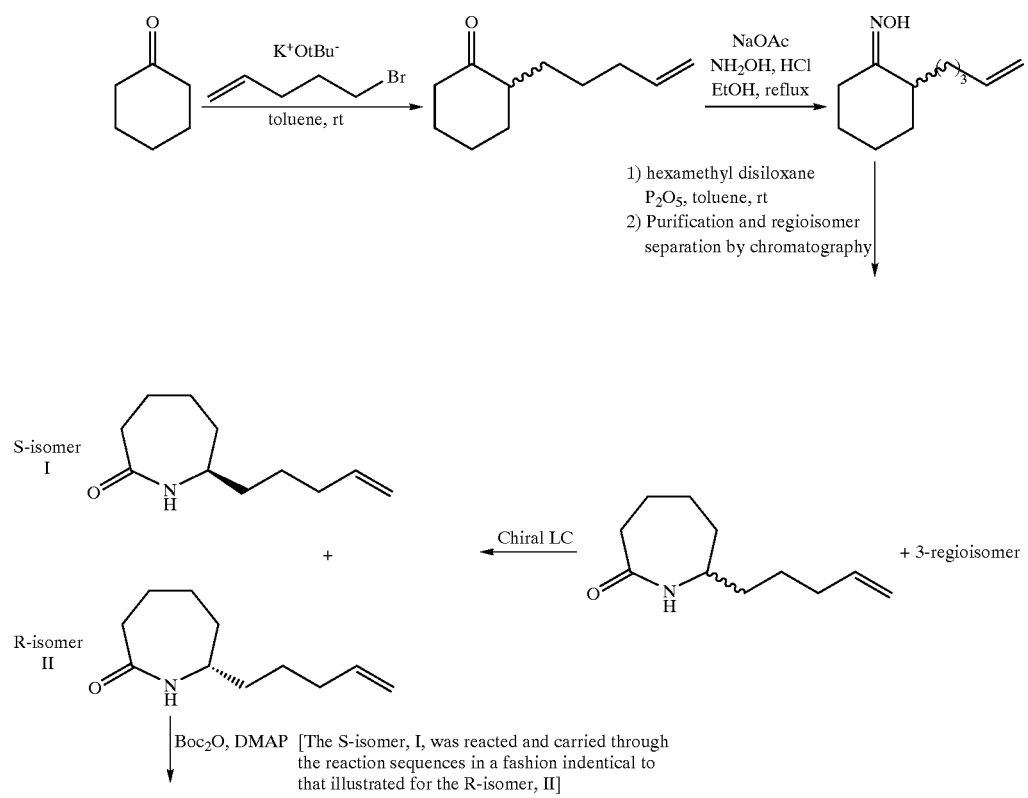

Scheme 1:

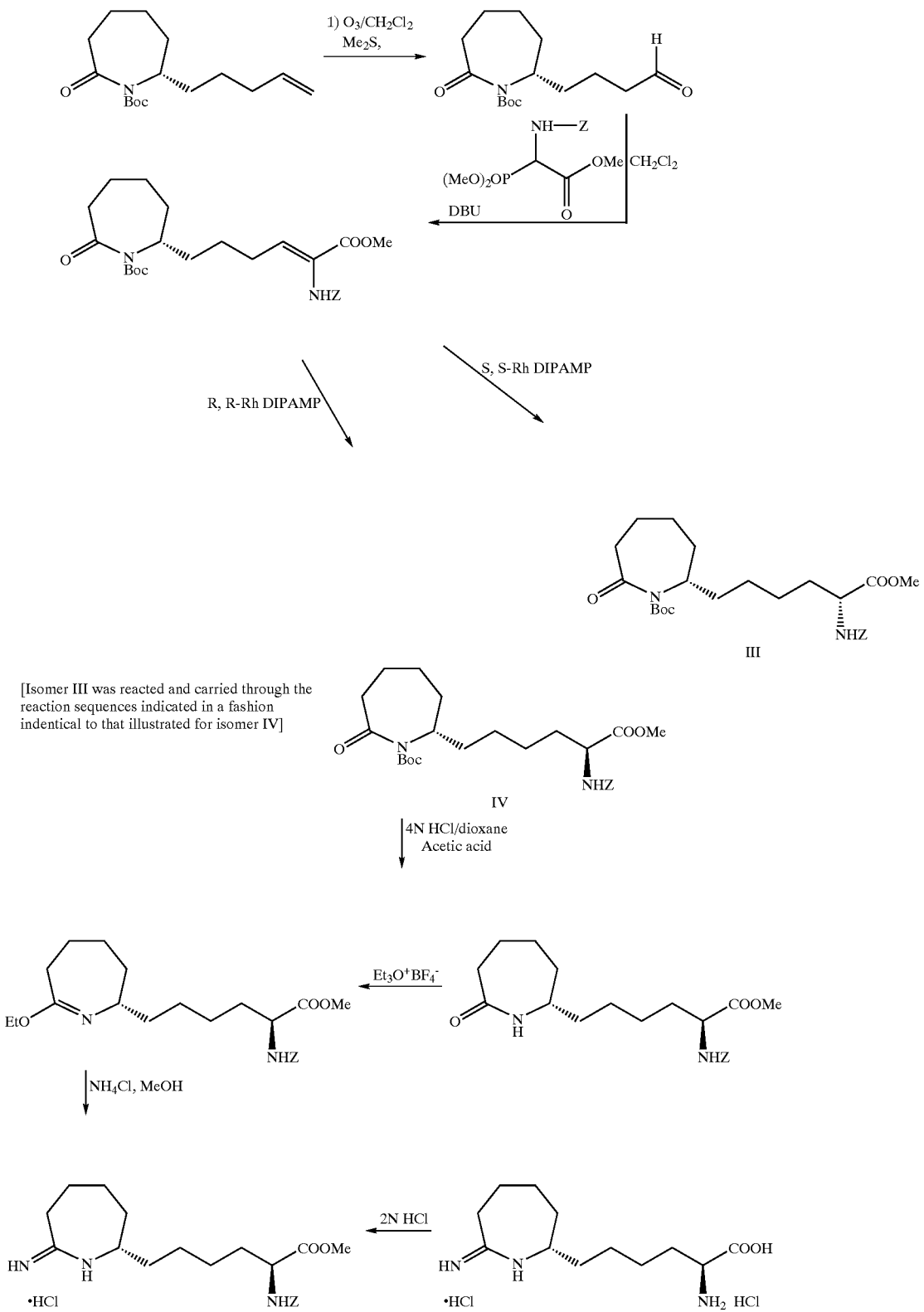

Scheme 2:
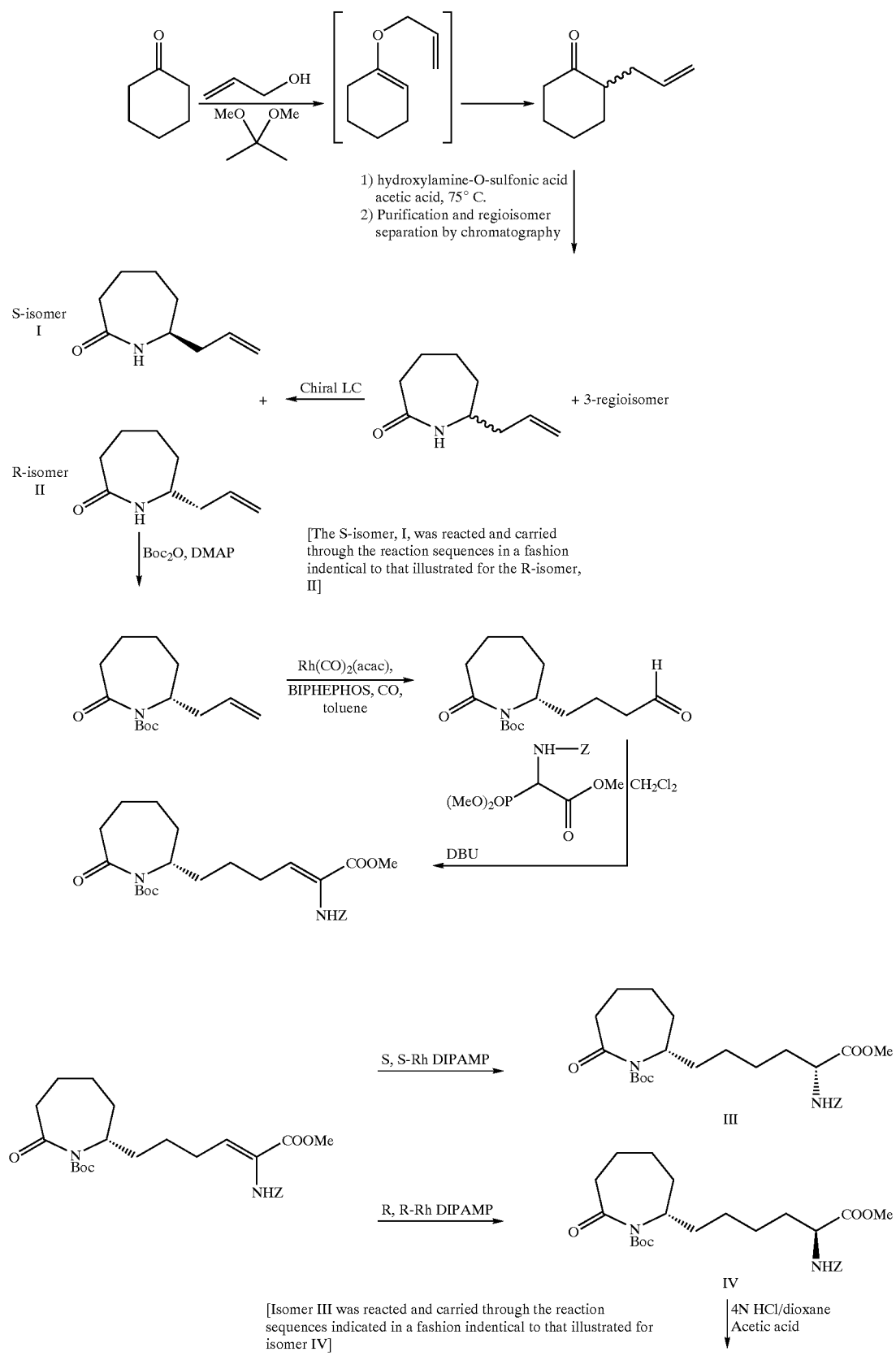

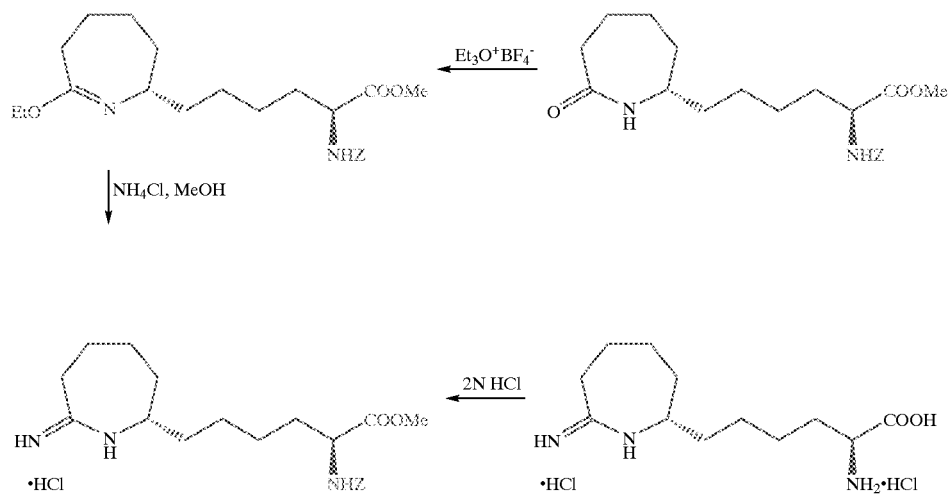
Scheme 3:
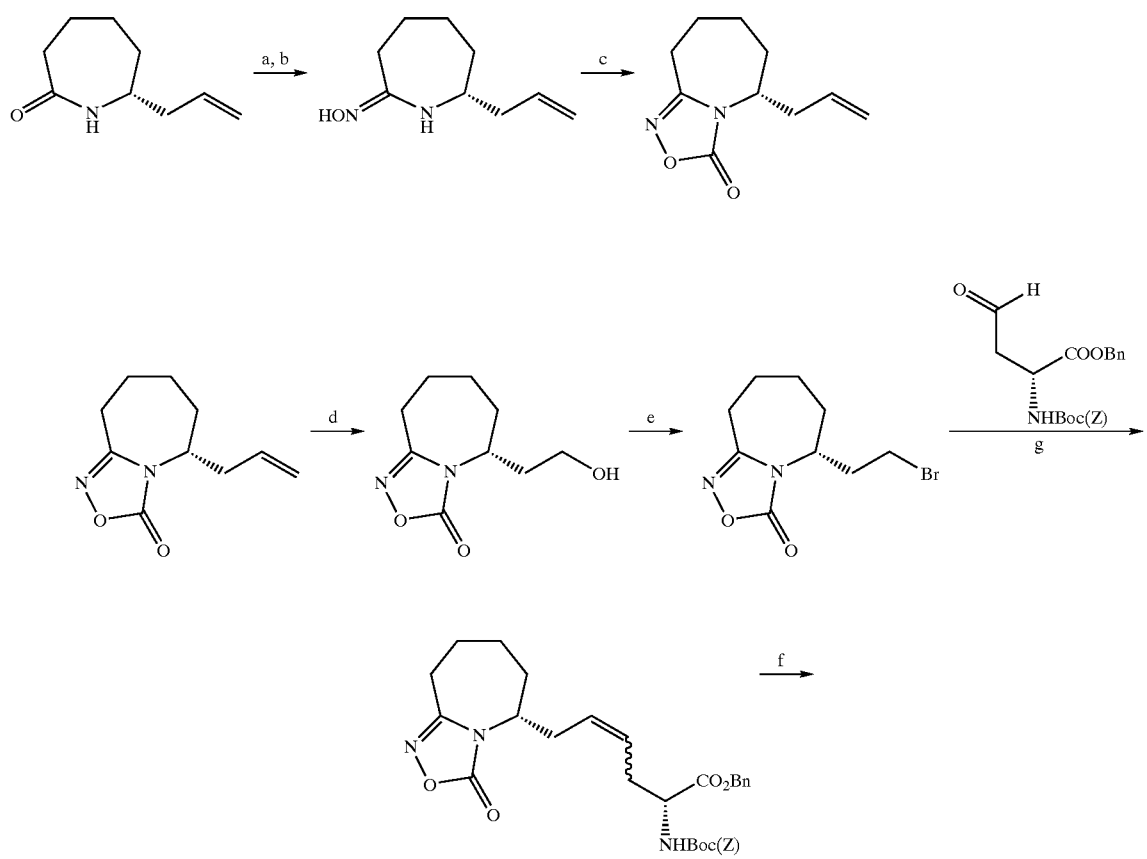

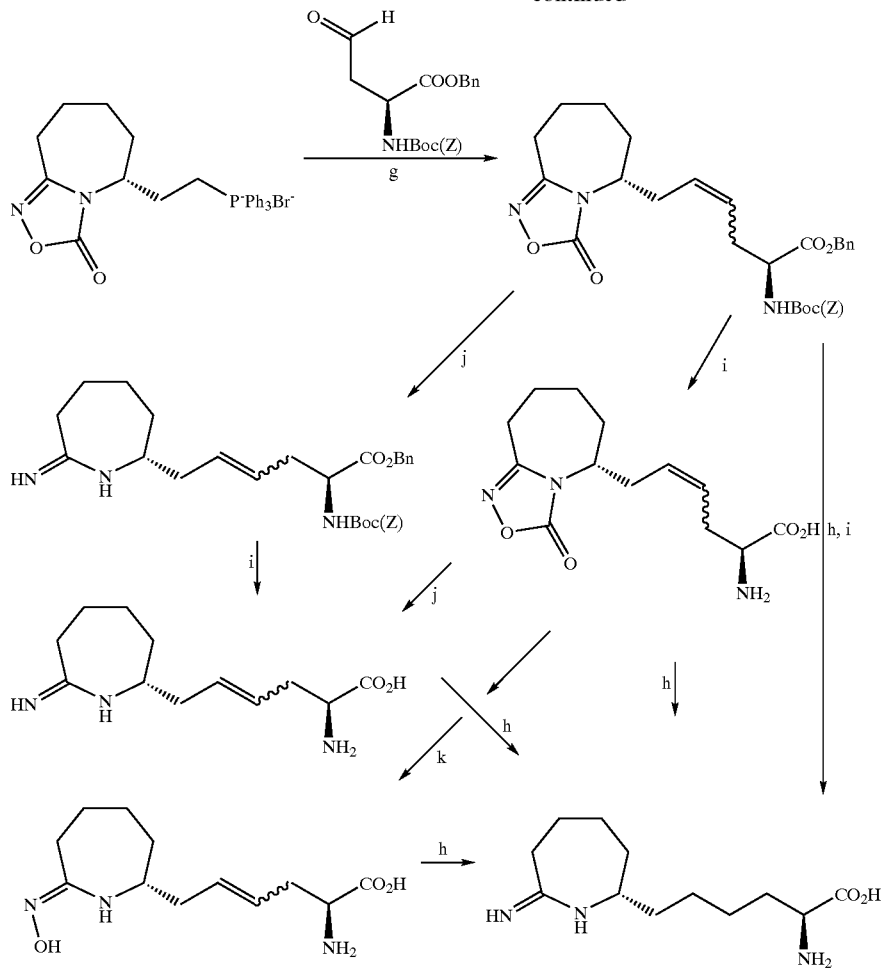

a) Meerwein's reagent. b) Hydroxylamine hydrochloride. c) 1,1'-Carbonyldiimidazole. d) i. $O_3$. ii.$NaBH_3$. e) $PPh_3$/$CBr_4$. f) $PPh_3$, reflux. g) Wittig reaction. h) Hydrogenation. i) HCl. j) Zn, HOAc. k) Aqueous KOH.

The following examples are provided to illustrate the present invention and are not intended to limit the scope thereof. Those skilled in the art will readily understand that known variations of the conditions and processes of the following preparative procedures can be used to prepare these compounds.

EXAMPLE 1

(αR,2S)-α-aminohexahydro-7-imino-1H-azepine-2-hexanoic acid, trihydrate hydrochloride

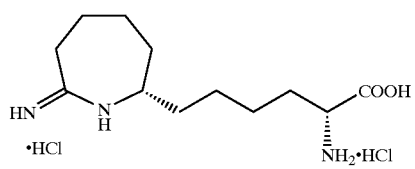

EXAMPLE 1a

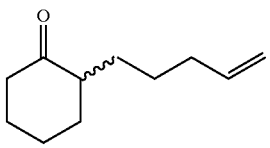

A three neck 3 L flask was purged with nitrogen before it was charged with cyclohexanone (1.27 mol, 132 mL) and 500 mL of toluene. This stirred mixture was cooled to 0° C. and 157.2 g (1.1 eq) of potassium t-butoxide was added. After stirring this mix for 1 hr, a color and texture change was noted before a solution of 5-pentenyl bromide (1.27 mol, 136 mL) in 100 mL toluene was added dropwise over 1 h to the mechanically stirred reaction mixture. The reaction mixture was allowed to warm to 25° C. and stir overnight. It was then diluted with 800 mL of 1 N $KHSO_4$ and the organic phase was dried ($MgSO_4$), filtered and evaporated to dryness to yield 208.5 g of crude product. This material was then purified by vacuum distillation (under water aspirator pressure) to give the title product in 47% yield.

$^1$H NMR ($CDCl_3$, δ ppm): 1.0–2.4 (m, 13H), 4.9–5.1 (m, 2H), 5.7–5.9 (m, 1H).

EXAMPLE 1b

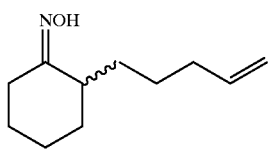

The product of Example 1a (93.67 g, 0.563 mole) along with EtOH (600 mL), water (300 mL), NaOAc (101.67 g, 1.24 mole), and NH$_2$OH.HCl (78.31 g, 1.13 mole) were combined in a three neck 3 L flask. This stirred reaction mixture was refluxed for 16 h and then stirred at 25° C. for another 24 h. All solvent was removed under reduced pressure and the residue was partitioned between diethylether (Et$_2$O, 500 mL) and water (200 mL). The aqueous layer was extracted 3×200 mL ether. The combined organic layers were dried over MgSO$_4$, filtered, and stripped in vacuo to give the title oxime (121.3 g, 100% crude yield).

$^1$H NMR (CDCl$_3$, δ ppm): 1.2–2.6 (m, 13H), 4.9–5.1 (m, 2H), 5.7–5.9 (m, 1H).

EXAMPLE 1c

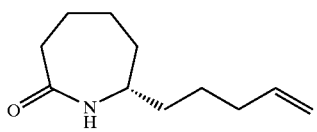

A three neck 3 L flask was purged with nitrogen and then charged with hexamethydisiloxane (471.7 mL, 2.2 moles), toluene (500 mL), and phosphorous pentoxide (203.88 g, 1.4 moles). This heterogeneous mixture was refluxed until a clear solution was obtained (about 1.5 h). After cooling this mixture to room temperature, the oxime product of Example 1b (102.1 g, 0.563 moles) in 200 mL of toluene was added to the above reaction mixture over a 1 h period at 25° C. The reaction mixture was stirred for another 4–6 h (checked by TLC: 50% EA in Hex, I$_2$) before it was poured into ice water with thorough mixing. To this ice slurry mixture was added 250 g of NaCl and the resulting mixture was adjusted to pH 5 by adding solid potassium carbonate. This slurry was extracted with 3×500 mL of diethylether (Et$_2$O) and the combined organic fractions were dried over MgSO$_4$, filtered and stripped in vacuo to give the crude mixture of regioisomeric lactams (84.6 g).

EXAMPLE 1d

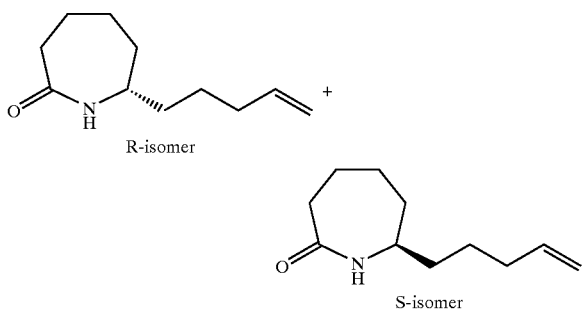

The product of Example 1c was then subjected to chromatography (silica:acetonitrile) for purification and regioisomeric separation. From the crude sample, the 7-pentenyl regioisomer was isolated in 50% yield and after chiral chromatography, the desired single enantiomers were isolated in 43% yield each.

R-isomer:

Elemental analyses Calcd for C$_{11}$H$_{19}$NO: C, 71.99; H, 10.57; N, 7.63. Found: C, 71.97; H, 10.58; N, 7.52

$^1$H NMR (CDCl$_3$, δ ppm): 1.3–1.6 (m, 7H), 1.75–1.9 (m, 2H), 1.95–2.15 (m, 3H) 2.4–2.5 (m, 2H), 3.25–3.35 (m, 1H), 4.95–5.05 (m, 2H), 5.7–5.85 (m, 1H).

$^{13}$C NMR (CDCl$_3$, δ ppm): 23.166, 25.169, 29.601, 33.209, 35.475, 35.624, 36.783, 53.600, 114.976, 137.923, 177.703

[α]$^{25}$=+26.9° (CHCl$_3$) at 365 nm.

S-isomer:

Elemental analyses Calcd for C$_{11}$H$_{19}$NO: C, 71.99; H, 10.57; N, 7.63. Found: C, 72.02; H, 10.61; N, 7.57

$^1$H NMR (CDCl$_3$, δ ppm): 1.3–1.6 (m, 7H), 1.75–1.9 (m, 2H), 1.95–2.15 (m, 3H 2.4–2.5 (m, 2H), 3.25–3.35 (m, 1H), 4.95–5.05 (m, 2H), 5.7–5.85 (m, 1H).

$^{13}$C NMR (CDCl$_3$, δ ppm): 23.187, 25.178, 29.630, 33.230, 35.526, 35.653, 36.778, 53.621, 115.032, 137.914, 177.703

[α]$^{25}$=−25.7° (CHCl$_3$) at 365 nm.

EXAMPLE 1e

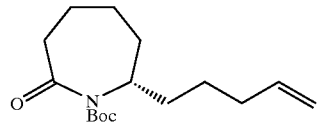

The R-isomer product of Example 1d (102.1 g, 0.56 mol), dry THF (800 mL), DMAP (68.9 g, 0.56 mol), Di-t-butyl dicarbonate (Boc$_2$O, 99 g, 0.45 mol) were combined in a three neck 3 L flask purged with argon. The reaction mixture was warmed to 70° C. within 30 min before an additional 52.8 g of Boc$_2$O and 200 mL of dry THF were added. After 30 min. another 32 g of Boc$_2$O was added and the mixture was stirred for 1 h at 70° C. Another 36 g of Boc$_2$O was added and the mixture was stirred for 1 h. The reaction mixture was cooled to room temperature and stripped of THF at 18° C. to 20° C. under reduced pressure. A precipitate was filtered and washed with 100 mL of ethylacetate (EA) and discarded (~45 g). The EA filtrate was diluted with 500 mL of additional EA before it was washed with 500 mL of 1N KHSO$_4$, 500 mL of saturated aq. NaHCO$_3$, and 500 mL of brine and then dried over anhydrous Na$_2$SO$_4$ for 12 h. This EA extract was then treated with 20 g of DARCO, filtered through celite topped with MgSO$_4$, and concentrated in vacuo to give 150 g of title product as a dark brown oil.

$^1$H NMR (CDCl$_3$, δ ppm): 1.3–1.6 (m, 4H), 1.5 (s, 9H), 1.6–1.9 (m, 6H), 1.95–2.05 (m, 2H), 2.5–2.7 (m, 2H), 4.2–4.25 (m, 1H), 4.95–5.05 (m, 2H), 5.7–5.85 (m, 1H).

EXAMPLE 1f

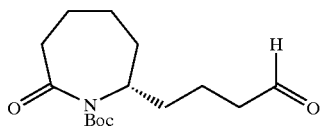

A three neck 3 L flask containing the product of Example 1e (150 g, 0.533) dissolved in 3 L of $CH_2Cl_2$ was cool to −78° C. A stream of $O_3$ was passed through the solution for 2.5 h until the color of the reaction mixture turned blue. Argon was then bubbled through the solution maintained at −60° C. to −70° C. until the solution became clear and colorless (~30 min.). Dimethylsulfide (DMS, 500 mL) was then added before the reaction was brought to reflux and this reflux was continued for 24 h. Another 100 mL of DMS was added and reflux was continued for 12 h. Another 100 mL of DMS was added and reflux continued for an additional 12 h. The solvent and excess DMS were then stripped on a rotary evaporator at 20° C. The residual yellow oil obtained was diluted with 500 mL of DI water and extracted with 3×300 mL of EA. The EA layer was dried over anhydrous $MgSO_4$, treated with 20 g of DARCO, filtered through a thin layer of celite topped with anhydrous $MgSO_4$, and stripped of all solvent under reduced pressure to yield 156 g of the crude title product as orange yellow oil.

$^1$H NMR (CDCl$_3$, δ ppm): 1.3–1.6 (m, 4H), 1.5 (s, 9H), 1.6–1.9 (m, 6H), 2.45–2.75 (m, 4H), 4.2–4.25 (m, 1H), 9.75 (s, 1 1H).

EXAMPLE 1g

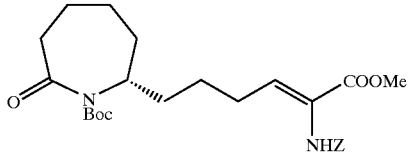

To a sample of N-(Benzyloxycarbonyl)-alpha-phosphonoglycine trimethyl ester (160 g, 0.48 mol) dissolved in 1 L of dichloromethane ($CH_2Cl_2$) and cooled to 0° C. was added a solution of DBU (110.29 g, 0.72 mol) in 100 mL of $CH_2Cl_2$. This clear colorless reaction mixture was stirred for 1 h at 0° C. to 6° C. before the Boc-aldehyde product of Example 1f (150 g, 0.53 mol) in 600 mL of $CH_2Cl_2$ was added drop wise at −5° C. to −1° C. The reaction mixture was stirred for 30 min. at this temperature before it was slowly warmed to 10° C. in approximately 1 h. The reaction mixture was washed with 1N $KHSO_4$ (500 mL), saturated aq. $NaHCO_3$ (200 mL) and 50 aq. NaCl (200 mL). The organic layer was then dried over anhydrous $MgSO_4$, treated with 40 g of DARCO, filtered through a thin layer of celite topped with anhydrous $MgSO_4$, and concentrated to give 258 g of the crude title product as an yellow oil. Chromatographic purification of this material gave 130 g (55%) of the pure title product.

Elemental analyses Calcd for $C_{26}H_{36}N_2O_7$: C, 63.96; H, 7.42; N, 5.77. Found: C, 63.42; H, 8.16; N, 5.31.

$^1$H NMR (CDCl$_3$, δ ppm): 1.25 (m, 2H), 1.5 (s, 9H), 1.51–1.9 (bm, 8H), 2.25 (m 2H), 2.5 (m, 1H), 2.65 (m, 1H), 3.75 (s, 3H), 4.12 (m, 1H), 5.15 (s, 2H), 6.3 (bs, 1H), 6.55 (t, 1H), 7.45 (m,5H).

$^{13}$C NMR (CDCl$_3$, δ ppm): 14.04, 22.62, 23.46, 24.08, 25.27, 27.89, 27.92, 28.34, 28.95, 31.81, 31.86, 32.05, 39.18, 52.31, 54.65, 67.27, 82.62, 128.07, 128.18, 128.46, 135.98, 136.82, 154.50, 164.92, 176.68.

$[α]^{25}$=+10.9° (CHCl$_3$) at 365 nm.

EXAMPLE 1h

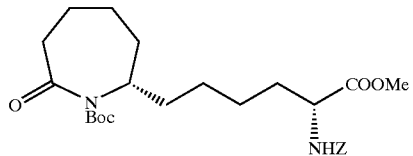

To a MeOH (1 L) solution of the product of Example 1g (91.3 g, 0.19 mol) was added 2.5 g of S,S-Rh-DIPAMP catalyst followed by hydrogen. The hydrogenation was carried out at 25° C. in 1.5 h in a Parr apparatus. The reaction mixture was filtered through celite before concentrating to provide the crude title product (90 g, 98%) as a brown oil.

$^1$H NMR (CDCl$_3$, δ ppm): 1.35 (m, 4H), 1.5 (s, 9H), 1.55–1.95 (m, 10H), 2.4–2.7 (m, 2H), 3.75 (s, 3H), 4.2 (m, 1H), 4.4 (m, 1H), 5.1 (m, 2H), 5.35 (d, 1H), 7.35 (m, 5H).

EXAMPLE 1i

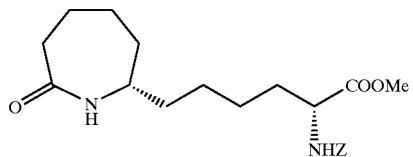

To a solution of the product of Example 1 h (90 g,) in 200 mL of glacial acetic acid was added 200 mL of 4N HCl in dioxane. The reaction mixture was stirred at 25° C. for 20 min. before it was stripped of all solvent under reduced pressure at 40° C. to give a red brown oil. This oily product was treated with 500 mL of water and extracted 2×300 mL of dichloromethane. The combined organic layer was washed with satd. sodium bicarbonate solution (100 mL), dried over magnesium sulfate, filtered and stripped of all solvent to give the crude title product. This material was chromatographed to provide 45 g (62%) of the pure title product.

Elemental analyses Calcd for $C_{21}H_{30}N_2O_5$: C, 64.02; H, 7.68; N, 7.17. Found: C, 63.10; H, 7.88; N, 6.60.

$^1$H NMR (CDCl$_3$, δ ppm): 1.2–2.0 (m, 14H), 2.45 (t, 2H), 3.25 (m,1H), 3.75 (s, 3H), 4.38 (m, 1H), 5.1 (s, 2H), 5.3 (d, 1H), 5.45 (bs, 1H), 7.35 (m, 5H).

$^{13}$C NMR (CDCl$_3$, δ ppm): 14.09, 23.11, 24.89, 25.41, 29.53, 32.33, 35.52, 35.79, 36.68, 52.26, 53.51, 53.55, 53.60, 60.26, 66.86, 127.97, 128.05, 128.40, 136.18, 155.85, 172.85, 177.80.

$[α]^{25}$=−9.9° (CHCl$_3$) at 365 nm.

EXAMPLE 1j

To a 45.0 g (0.115 mol) sample of the product of Example 1i in 300 mL of dichloromethane purged with argon was added 23.0 g (0.121 mol) of triethyloxonium tetrafluoroborate. This mixture was stirred for 1 h at 25° C. before 150 mL of satd. aq. sodium bicarbonate solution was added. The dichloromethane layer was separated, washed with 150 mL of 50% aq. NaCl solution, dried over sodium sulfate, filtered through celite and concentrated at 25° C. to give a clear yellow oil, 47.0 g (97%) of the title product Elemental analyses Calcd for $C_{23}H_{34}N_2O_5$: C, 60.01; H, 8.19; N, 6.69. Found: C, 65.13; H, 8.45; N, 6.64.

$^1$H NMR (CDCl$_3$, δ ppm): 1.2 (t, 3H), 1.25–1.74 (m, 12H), 1.75–1.95 (m, 2H), 2.2–2.3 (m, 1H), 2.4–2.5 (m, 1H), 3.1 (m, 1H), 3.7 (s, 3H), 3.9–4.0 (m, 2H), 4.35 (m, 1H), 5.1 (s, 2H), 5.25 (d, 1H), 7.35 (m, 5H).

$^{13}$C NMR (CDCl$_3$, δ ppm): 14.23, 23.38, 25.01, 25.21, 26.10, 30.24, 32.16, 32.77, 33.92, 39.15, 52.22, 53.91, 58.05, 60.19, 66.92, 128.11, 128.33, 128.48, 136.27, 155.83, 166.29, 173.11, 177.64.

EXAMPLE 1k

To 7.0 g (0.130 mol) of ammonium chloride in 500 mL methanol was added 31.2 g of the title material of Example 1j (45.0 g, 0.107 mol). The reaction was refluxed at 65° C. for 5 h before all solvent was removed under reduced pressure to yield 40 g (87%) of the crude product as a foamy viscous mass. This material was purified by column chromatography to provide 37 g (81%) of the title product.

Elemental analyses Calcd for $C_{21}H_{31}N_3O_4$: C, 59.22; H, 7.57; N, 9.86; Cl, 8.32. Found for $C_{21}H_{31}N_3O_4$+1.2 HCl+0.5 H$_2$O: C, 57.20; H, 7.99; N, 9.66; Cl, 9.62.

IR (Neat, λ max cm$^{-1}$): 2935, 1716, 1669.

$^1$H NMR (CDCl$_3$, δ ppm): 1.2–2.0 (m, 13H), 2.5 (t, 1H), 2.95 (m, 1H), 3.4 (bs, 1H), 3.7 (s, 3H), 4.3 (m, 1H), 5.1 (s, 2H), 5.55 (d, 1H), 7.3 (m, 5H), 8.75 (bs,1H), 8.9 (bs, 1H), 9.5 (s, 1H).

$^{13}$C NMR (CDCl$_3$, δ ppm): 23.20, 24.95, 25.22, 28.94, 31.80, 32.05, 33.75, 34.89, 52.33, 53.76, 56.07, 66.83, 127.93, 128.04, 128.43, 136.26, 156.00, 172.24, 172.87.

Mass (ESI): M/Z, 390.

[α]$^{25}$=+31.5° at 365 nm.

EXAMPLE 1

The title product of Example 1k (36.0 g, 0.084 mol) in 1 L of 2.3 N HCl was refluxed for 3 h. After cooling to room temperature, the solution was washed with 2×150 mL of CH$_2$Cl$_2$ and then stripped of all solvent in vacuo to give 25.6 g (96%) of the title amino acid product as a pale yellow foam.

Elemental analyses Calcd for $C_{12}H_{23}N_3O_2$. 2HCl: C, 46.02; H, 8.01; N, 13.39; Cl 22.45. Found for $C_{12}H_{23}N_3O_2$+ 2.2 HCl+0.1 H$_2$O: C, 42.76; H,8.02; N, 12.41; Cl, 22.79.

IR (Neat, λ max, cm$^{-1}$): 2930, 2861, 1738,1665.

$^1$H NMR (CD$_3$OD, δ ppm): 1.3–2.5 (m, 16H), 2.6 (dd, 1H), 2.8 (t, 1H), 3.65 (m, 1H), 4.0 (t, 1H), 7.85 (s, 1H), 8.85 (s, 1H), 8.95 (s, 1H).

$^{13}$C NMR (CD$_3$OD, δ ppm): 24.49, 25.67, 26.33, 29.71, 31.26, 32.45, 35.04, 35.87, 53.73, 57.21, 171.77, 173.96.

UV, 282 nm, abs 0.015.

Mass (M$^{+1}$)=242.

[α]$^{25}$=−47.4° (MeOH) at 365 nm.

ee=91% as determined by CE at λ=214 nm.

EXAMPLE 2

(αS,2R)-α-aminohexahydro-7-imino-1H-azepine-2-hexanoic acid, trihydrate hydrochloride

EXAMPLE 2a

The S-isomer product of Example 1d (5.45 g, 0.030 mol) was converted to its Boc derivative by the method of Example 1e. After chromatography, this reaction yielded 6.3 g (75%) of the desired title product.

$^1$H NMR (CDCl$_3$, δ ppm): 1.3–1.6 (m, 4H), 1.5 (s, 9H), 1.6–1.9 (m, 6H), 1.95–2.05 (m, 2H), 2.5–2.7 (m, 2H), 4.2–4.25 (m, 1H), 4.95–5.05 (m, 2H), 5.7–5.85 (m, 1H).

EXAMPLE 2b

The product of Example 2a (6.3 g, 0.025 mol) was ozonized by the method of Example 1f to produce 8.03 g of the crude title aldehyde that was used without further purification.

$^1$H NMR (CDCl$_3$, δ ppm): 1.3–1.6 (m, 4H), 1.5 (s, 9H), 1.6–1.9 (m, 6H), 2.45–2.75 (m, 4H), 4.2–4.25 (m, 1H), 9.75 (s, 1H).

EXAMPLE 2c

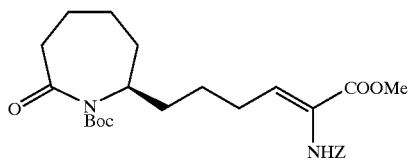

The product of Example 2b (8.03 g, 0.024 mol) was condensed with N-(Benzyloxycarbonyl)-alpha-phosphonoglycine trimethyl ester (7.9 g, 0.024 mol) utilizing the procedure of Example 1g to produce 4.9 g (44%) of the desired title product after chromatography.

$^1$H NMR (CDCl$_3$, δ ppm): 1.25 (m, 2H), 1.5 (s, 9H), 1.51–1.9 (bm, 8H), 2.25 (m, 2H), 2.5 (m, 1H), 2.65 (m, 1H), 3.75 (s, 3H), 4.15–4.25 (m, 1H), 5.15 (s, 2H), 6.3–6.4 (bs, 1H), 6.45–6.55 (t, 1H), 7.3–7.4 (m, 5H).

EXAMPLE 2d

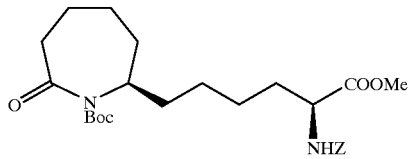

The product of Example 2c (4.8 g, 0.010 mol) was reduced in the presence of R,R-Rh-DIPAMP catalyst by the method of Example 1h to produce 2.9 g (60%) of the desired title product after chromatography.

EXAMPLE 2e

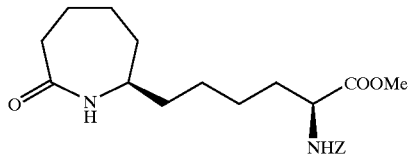

The product of Example 2d (2.9 g, 0.006 mol) was deprotected by treatment with HCl using the method of Example 1i to produce 2.3 g (100%) of the desired title product.

$^1$H NMR (CDCl$_3$, δ ppm): 1.3–2.0 (m, 14H), 2.45 (t, 2H), 3.25 (m, 1H), 3.75 (s, 3H), 4.38 (m, 1H), 5.1 (s, 2H), 5.3 (d, 1H), 5.45 (bs, 1H), 7.35 (m, 5H).

EXAMPLE 2f

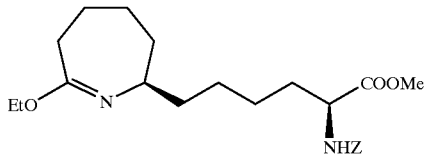

The product of Example 2e (0.56 g, 0.0015 mol) was alkylated with triethyloxonium tetrafluoroborate using the method of Example 1j to produce 0.62 g (98%) of the desired title product.

EXAMPLE 2g

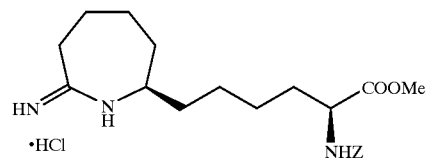

The product of Example 2f (0.62 g, 0.0015 mol) was treated with ammonium chloride in methanol using the method of Example 1k to produce 0.50 g (88%) of the desired title product after chromatographic purification.

EXAMPLE 2h

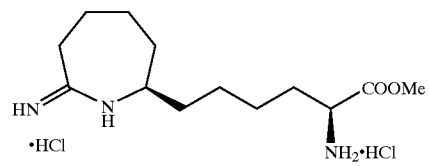

The product of Example 2g (0.37 g, 0.0009 mol) dissolved in MeOH was added to a Parr hydrogenation apparatus. To this vessel was added a catalytic amount of 5% Pd/C. Hydrogen was introduced and the reaction was carried out at room temperature at pressure of 5 psi over a 7 hr period. The catalyst was removed by filtration and all solvent was removed under reduced pressure from the filtrate to produce 0.26 g (quantitative) of the desired title product.

EXAMPLE 2

A solution of the product of Example 2h dissolved in 2N HCl (30 mL) was maintained at reflux for 2 h before it was cooled to room temperature. All solvent was removed under reduced pressure and the residue was dissolved in 50 mL of water. This solution was again stripped of all solvent under reduced pressure before it was again dissolved in 12 mL of water and then lyophilized to generated 0.245 g (71%) of the title compound.

Elemental analyses Calcd for C$_{12}$H$_{23}$N$_3$O$_2$.2.3 HCl.1.9 H$_2$O: C, 40.10; H, 8.16; N, 11.69; Cl 22.69. Found for C$_{12}$H$_{23}$N$_3$O$_2$+2.1 HCl+0.7 H$_2$O: C, 40.27; H, 8.28; N, 11.62; Cl, 22.70.

$^1$H NMR (CD$_3$OD, δ ppm): 1.4–2.1 (m, 16H), 2.6 (dd, 1H), 2.8 (t, 1H), 3.65 (m, 1H), 4.0 (t, 1H), 7.85 (s, 1H), 8.45 (s, 1H), 8.9 (s, 1H).

$^{13}$C NMR (CD$_3$OD, δ ppm): 24.46, 25.64, 26.31, 29.69, 31.24, 32.54, 35.00, 35.83, 53.75, 57.20, 171.85, 173.93.

$[α]^{25}$=+25.7° (MeOH) at 365 nm.

EXAMPLE 3

(αR,2R)-α-aminohexahydro-7-imino-1H-azepine-2-hexanoic acid, trihydrate hydrochloride

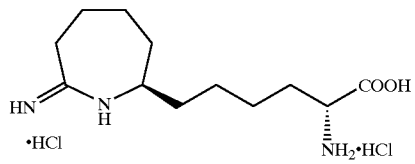

EXAMPLE 3a

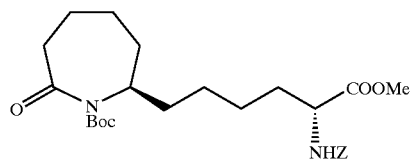

The product of Example 2c is reduced in the presence of S,S-Rh-DIPAMP catalyst by the method of Example 1h to produce the desired title product after chromatography.

EXAMPLE 3b

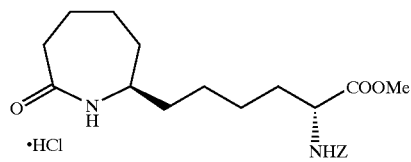

The product of Example 3a is deprotected by treatment with HCl using the method of Example 1i to produce the desired title product.

EXAMPLE 3c

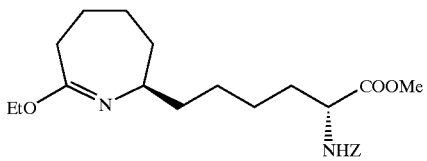

The product of Example 3b is alkylated with triethyloxonium tetrafluoroborate using the method of Example 1j to produce the desired title product.

EXAMPLE 3d

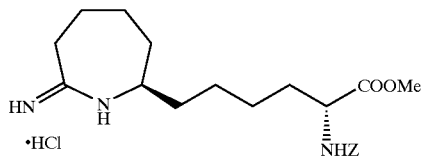

The product of Example 3c is treated with ammonium chloride in methanol using the method of Example 1k to produce the desired title product after chromatographic purification.

EXAMPLE 3

A solution of the product of Example 3d in 2N HCl is treated as described in Example 1 to generate the title compound.

EXAMPLE 4

(αS,2S)-α-aminohexahydro-7-imino-1H-azepine-2-hexanoic acid, trihydrate hydrochloride

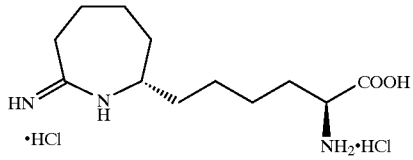

EXAMPLE 4a

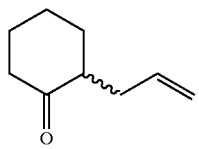

To a 22 L round bottom flask equipped with overhead stirrer, half moon shape paddle, heating mantle, thermocouple, and a silver vacuum jacketed distillation column (5 plates) was charged cyclohexanone (4500.0 g, 45.85 mol), acetone dimethyl acetal (5252.6 g, 50.43 mol), allyl alcohol (6390.87 g, 110.04 mol) and p-toluene sulfonic acid (PTSA) (0.256 g, 0.001 mol). After the stirring was started (137 rpm) the pot was heated slowly with the initial set point being 70° C. Heating was increased step wise to a final pot temperature of 150° C. The decision to increase the reactor set point was made based on distillation rate. If the rate of distillate slowed or stopped, additional heat was applied. The additional heating to 150° C. allowed the Claisen rearrangement to occur. After the pot temperature was raised to 150° C. and no distillate was observed, the heating mantle was lowered and the reaction mixture allowed to cool to 130° C. The PTSA was then neutralized with 3 drops of 2.5 N NaOH. The vacuum stripping was then started with the heating mantle lowered away from the flask. Evaporative cooling was used to lower the pot temperature, and the pressure was gradually lowered to 40 mm Hg. When the pot temperature had decreased to ~100° C., the heating mantle was raised back into the proper position for heating. Unreacted cyclohexanone and low boiling impurities were distilled off. The pot temperature was slowly raised (the maximum temperature deferential between the pot and vapor was ~12° C.). The product was isolated at 109–112° C. @ 40 mm Hg. Typical yields were 40–45%. Fractions which were <95% by area (GC) were combined and redistilled to afford the title product in a total yield of 55%.

$^1$H NMR (CDCl$_3$, δ ppm): 5.8–5.6 (m, 1H), 4.8–5.0 (m, 2H), 2.5–2.4 (m, 1H), 2.3–2.1 (m, 3H), 2.1–1.2 (m, 7H).

$^{13}$C NMR (CDCl$_3$, δ ppm): 212.53, 136.62, 116.32, 50.39, 42.18, 33.91, 33.52, 28.09, 25.10.

GC/MS m/z=138.

EXAMPLE 4b

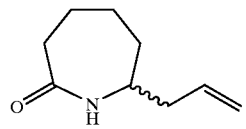

Hydroxyl amine-O-sulfonic acid (91.8 g) dissolved in acetic acid (470 g) was added to a 1 L Bayer flask equipped with a mechanical stirrer, thermocouple, condenser chilled to 0° C., and an addition funnel and heated to 70° C. The allyl cyclohexone (100 g) was added dropwise in approximately 40 min to the above solution while maintaining the temperature between 70 and 78° C. During the addition, the reaction appearance changed from a white slurry to a clear orange solution. After the addition, the reaction was heated and stirred for an additional 5 h at 75° C. An IPC sample was taken each hour. After the reaction was complete, the acetic acid was stripped at 50° C. under reduced pressure on a rotary evaporator. Water (200 mL) was then added to the residue and the solution extracted with toluene (2×300 mL). The organic layers were combined, treated with water (150 ml) and stirred for 10 min. A sodium hydroxide solution (79.4 g of 50 solution) was added until the aqueous layer turned basic (pH 12). The neutralization was carried out in the reactor by controlling the temperature below 40° C. The layers were then separated and the toluene layer was passed through a filter to remove any solids or tarry material. The organic solution was then stripped at 50° C. under reduced pressure on a rotary evaporator. The residue was taken up in a mixture of toluene (510 mL) and heptanes (2040 mL) and heated to 60° C. in a 3 L reactor. A clear yellow-orange solution was obtained. The title product began to crystallize at 53° C. as the solution was slowly cooled to 5° C. while being stirred. The solid was filtered, washed with heptanes (50 mL) and dried over night at 40° C. under house vacuum to produce 66.3 g (60%) of title product as off-white crystals obtained. A portion of this material was recrystallized from toluene and heptane to generate the title product as a white crystalline solid.

$^1$H NMR (CDCl$_3$, δ ppm): 5.8–5.6 (m, 1H), 5.5 (bs, 1H), 4.8–5.0 (m, 2H), 3.4–3.3 (m, 1H), 2.5–2.3(m, 2H), 2.3–2.1 (m, 2H) 2.0–1.2 (m, 6H)

$^{13}$C NMR (CDCl$_3$, δ ppm): 117.73, 133.83, 119.31, 52.88, 40.95, 37.20, 35.75, 29.96, 23.33.

GC/MS (EI mode)=153.

m.p.=97–99° C.

EXAMPLE 4c

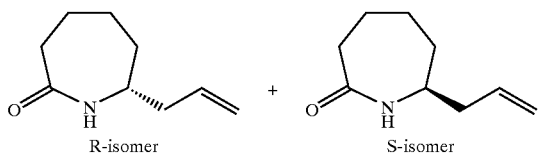

R-isomer + S-isomer

The racemic product mixture of Example 4b was subjected to chiral chromatographic separation on a Chiralpac AS 20 um column eluting with 100% acetonitrile. A 220 nM wavelength was employed in the detector. A sample loading of 0.08 g/mL of acetonitrile was used to obtain 90% recovery of separated isomers each with >95% ee. A portion of the R-isomer material was recrystallized from toluene and hep-tane to generate the R-isomer title product as a white crystalline solid.

R-isomer: m.p.=81–82° C.

EXAMPLE 4d

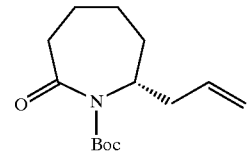

A five necked flat bottom flask equipped with dropping funnel, thermometer and mechanical overhead stirrer was evacuated and purged with nitrogen three times. The R-isomer product lactam of Example 4c (100.0 g, 0.653 mol), DMAP (7.98 g, 65 mmol) and N-diisopropylethyl amine (Hünigs base, 113.3 g, 0.876 mol) were dissolved in toluene (350 mL) and Di-tert-butyl dicarbonate (170.2 g, 0.78 mol) dissolved in toluene (100 mL) was added. (Note: the reaction works better, when 2.0 eq of Hünigs base were used). The mixture was heated to 65° C. (Note: Steady offgasing during the reaction was observed). After 1.5 h another 86.25 g of Di-tert-butyl-dicarbonate (0.395 mol) dissolved in toluene (50 mL) were added. Heating was continued for 17 h and IPC by HPLC showed 75 conversion. Another 42.78 g of Di-tert-butyl dicarbonate (0.196 mol) in toluene (30 mL) were added and the brown mixture was heated 5.5 h. After cooling to ambient temperature, the mixture was treated with 4M HCl (215 mL), and the aqueous layer was extracted with toluene (2×80 mL). The combined organic layers were washed with NaHCO$_3$ (170 mL) and 250 ml of water (Note: the internal temperature during the quench was controlled by external cooling with ice/water). Gas evolution was observed. The organic layer was evaporated to give 257.4 g brown liquid. This crude material was purified by plug filtration over SiO$_2$ (950 g) using toluene/EtOAc 9/1 (6 L) and toluene/AcOEt 1/1 (0.5 L) as eluent giving 139.5 g (51%) of the yellow liquid title product.

EXAMPLE 4e

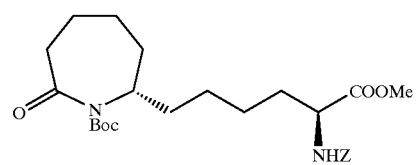

EXAMPLE 4e-1

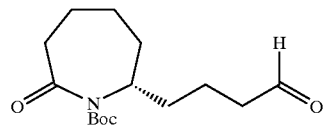

Example 1f

Into a 2-L stainless steel autoclave equipped with baffles and a six-bladed gas dispersing axial impeller was charged Rh(CO)$_2$(acac) (0.248 g, 0.959 mmol), BIPHEPHOS (structure shown below and prepared as described in Example 13 of U.S. Pat. No. 4,769,498, 2.265 g, 2.879 mmol), the product of Example 4d (N-(tert-butoxycarbonyl)-S-7-allylcaprolactam

BIPHEPHOS

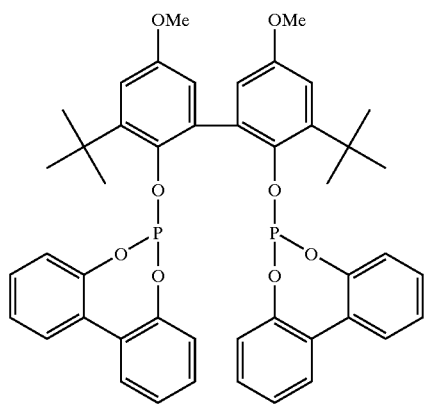

(242.9 g, 0.959 mol), and toluene (965 g). The reactor was sealed and purged 100% carbon monoxide (8×515 kPa). The reactor was pressurized to 308 kPa (30 psig) with 100% carbon monoxide and then a 1:1 CO/$H_2$ gas mixture was added to achieve a total pressure of 515 kPa (60 psig). With vigorous mechanical agitation, the mixture was heated to 50° C. with a 1:1 CO/$H_2$ gas mixture added so as to maintain a total pressure of about 515 kPa (60 psig). After 22 h, the mixture was cooled to about 25° C. and the pressure was carefully released. Vacuum filtration of the product mixture and evaporation of the filtrate under reduced pressure afforded a 267.7 g of a light yellow oil. Analysis by $^1$H NMR was consistent with essentially quantitative conversion of the starting material with about 96% selectivity to the corresponding aldehyde product of Example 1f. This oil was used without further purification in the following example.

$^1$H NMR (CDCl$_3$) δ1.47 (s, 9H), 1.6–1.80 (m, 9H), 1.84–1.92(m, 1H), 2.41–2.58 (m, 3H), 2.61–2.71 (m, 1H), 4.2 (d, J=5.2 Hz, 1H), 9.74 (s, 1H).

EXAMPLE 4e-2

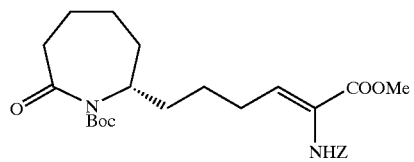

Example 1g

To a sample of N-(Benzyloxycarbonyl)-alpha-phosphonoglycine trimethyl ester (901.8 g, 2.7 mol) dissolved in CH$_2$Cl$_2$ and cooled to 0° C. was added a solution of DBU (597.7 g, 3.9 mol) in CH$_2$Cl$_2$. This clear colorless reaction mixture was stirred for 1 h at 0° C. to 6° C. before a sample of the Boc-aldehyde product Example 1f (812.0 g, 2.9 mol) in CH$_2$Cl$_2$ was added drop wise at −5° C. to −1° C. The reaction, work up, and purification was completed as described in Example 1g to give 1550 g of the title product of Example 1g containing a small amount of CH$_2$Cl$_2$.

EXAMPLE 4e

To a MeOH (1 L) solution of the product of Example 1g (100 g, 0.20 mol) was added 3 g of RR-Rh-DIPAMP catalyst. The hydrogenation was carried out at 25° C. in 1.5 h in a Parr apparatus. The reaction mixture was filtered through celite before concentrating to provide the crude Example 4e title product as a brown oil (100 g).

$^1$H NMR (CDCl$_3$, δ ppm): 1.35 (m, 4H), 1.5 (s, 9H), 1.6–1.9(m, 10H), 2.5–2.8 (m, 2H), 3.75 (s, 3H), 4.25 (m, 1H), 4.45 (m, 1H), 5.1 (m, 2H), 5.65 (d, 1H), 7.35 (m, 5H).

EXAMPLE 4f

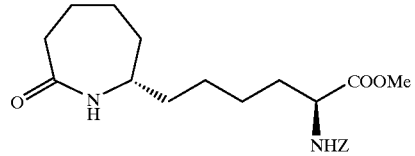

To a solution of the product of Example 1h (100 g) in 200 mL glacial acetic acid was added 25 mL 4N HCl in dioxane. The reaction mixture was stirred at 25° C. for 20 min. before it was stripped of all solvent under reduced pressure at 40° C. to give 105 g of red brown oil. This oily product was treated with 500 mL of water and extracted 2×300 mL of dichloromethane. The combined organic layer was washed with satd. sodium bicarbonate solution (100 mL), dried over magnesium sulfate, filtered and stripped of all solvent to give 99.9 g of the title product as a red brown oil.

$^1$H NMR (CDCl$_3$, δ ppm): 1.25–2.0 (m, 14H), 2.45 (t, 2H), 3.25 (m, 1H), 3.7 (s, 3H), 4.35 (m, 1H), 5.1 (s, 2H), 5.5 (d, 1H), 6.45 (bs, 1H), 7.35 (m, 5H).

ee=95% as determined by chiral HPLC.

EXAMPLE 4g

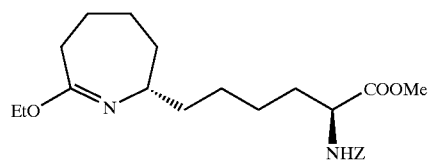

To a 30.0 g (0.077 mol) sample of the product of Example 4f in 600 mL dichloromethane purged with argon was added 15.7 g (0.082 mol) of triethyloxonium tetrafluoroborate. This mixture was stirred for 1 h at 25° C. before 300 mL of satd. aq. sodium bicarbonate solution was added. The dichloromethane layer was separated, washed with 300 mL 50% aq. NaCl solution, dried over sodium sulfate, filtered through celite and concentrate at 25° C. to give a clear yellow oil, 31.2 g (~97%) of the title product.

Elemental analyses Calcd for C$_{23}$H$_{34}$N$_2$O$_5$: C, 60.01; H, 8.19; N, 6.69. Found for C$_{23}$H$_{34}$N$_2$O$_5$+0.5 H$_2$O: C, 64.66; H, 8.24; N,6.59.

$^1$H NMR (CDCl$_3$, δ ppm): 1.2 5(t, 3H), 1.28–1.75 (m, 12H), 1.8–1.98 (m, 2H), 2.2–2.3 (m, 1H), 2.4–2.5 (m, 1H), 3.1 (m, 1H), 3.78 (s, 3H), 3.9–4.0 (m, 2H), 4.35 (m, 1H), 5.1 (s, 2H), 5.25 (d, 1H), 7.35 (m, 5H).

$^{13}$C NMR (CDCl$_3$, δ ppm): 14.27, 23.36, 25.21, 25.53, 26.09, 30.22, 32.15, 32.73, 33.90, 39.14, 52.21, 53.89, 58.04, 60.33, 66.89, 128.11, 128.35, 128.48, 136.29, 155.86, 166.30, 173.14, 177.69.

IR (Neat, λ max, cm$^{-1}$): 3295, 2920, 1739, 1680.

UV,257 nm, abs 0.015.

$[\alpha]^{25}$+39.8° (CHCl$_3$) at 365 nm.

EXAMPLE 4h

To 4.2 g (0.078 mol) of ammonium chloride in 500 mL methanol was added 31.2 g of the title material of Example 4g. The reaction was refluxed at 65° C. for 5 h before all solvent was removed under reduced pressure to yield 29 g (92%) of the crude product as a foamy viscous mass. This material was purified by column chromatography to provide 23 g (70%) of the title product.

Elemental analyses Calcd for $C_{21}H_{31}N_3O_4 \cdot 1HCl$) C, 59.28; H, 7.57; N, 9.89; Cl, 8.39. Found (For $C_{21}H_{31}N_3O_4$+ 1HCl+1H$_2$O): C, 56.73; H, 7.74; N, 9.40; Cl, 8.06.

IR (Neat, λ max cm$^{-1}$): 3136, 30348, 2935, 1716, 1669.

$^1$H NMR (CDCl$_3$, δ ppm): 1.3–2.05 (m, 13H), 2.5 (t, 1H), 2.98 (m, 1H), 3.4 (bs, 1H), 3.75 (s, 3H), 4.35 (m, 1H), 5.1 (s, 2H), 5.5 (d, 1H), 7.35 (m, 5H), 8.75 (s,1H), 9.0 (s, 1H), 9.5 (s, 1H).

$^{13}$C NMR (CDCl$_3$, δ ppm): 23.25, 25.01, 25.34, 29.01, 31.88, 32.26, 33.89, 35.06, 52.33, 53.73, 56.20, 66.89, 127.95, 128.06, 128.45, 136.27, 155.93, 172.27, 172.80.

UV, 257 nm, abs 0.009.

Mass (ESI): M/Z, 390.

$[\alpha]^{25}$=–42.8° (MeOH) at 365 nm.

ee=96% as determined by chiral HPLC.

EXAMPLE 4

The title product of Example 4h (23 g) in 500 mL 2N HCl was refluxed for 5 h. All solvent was then removed in vacuo and the residue redissolved in water was washed with 2×300 mL of CH$_2$Cl$_2$. The aqueous was then concentrated in vacuo to give 17 g (100%) of the light brown hygroscopic solid title product.

Elemental analyses Calcd for $C_{12}H_{23}N_3O_2 \cdot 2HCl$: C, 45.86; H, 8.02; N, 13.37; Cl 22.56. Found for $C_{12}H_{23}N_3O_2$+ 2.1 HCl+0.7 H$_2$O: C, 43.94; H, 8.65; N, 12.52; Cl, 22.23.

IR (Neat, λ max, cm$^{-1}$): 2936, 1742,1669.

$^1$H NMR (CD$_3$OD, δ ppm): 1.3–2.1 (m, 16H), 2.6 (dd, 1H), 2.8 (t, 1H), 3.65 (m, 1H), 4.0 (t, 1H), 7.85 (s, 1H), 8.4 (s, 1H), 8.95 (s, 1H).

$^{13}$C NMR (CD$_3$OD, δ ppm): 24.49, 25.67, 26.33, 29.71, 31.26, 32.45, 35.04, 35.87, 53.73, 57.21, 171.77, 173.96.

UV, 209 nm, abs 0.343.

Mass (M$^{+1}$)=242.

$[\alpha]^{25}$=+60.0° (MeOH) at 365 nm.

ee=92% as determined by CE at λ=210 nm.

EXAMPLE 5

(αR,2S)-α-aminohexahydro-7-imino-1H-azepine-2-hexanoic acid, trihydrate hydrochloride

EXAMPLE 5a

A solution of Example 4c (3.0 g, 0.015 mol) in methylene chloride and methanol (75/45 mL) was cooled to –78° C. in a dry ice bath. The reaction stirred as ozone was bubble through the solution at a 3 ml/min flow rate. When the solution stayed a consistent deep blue, the ozone was remove and the reaction was purged with nitrogen. To the cold solution was added sodium borohydride (2.14 g, 0.061 mol) very slowly to minimize the evolution of gas at one time. To the reaction was added glacial acetic acid slowly to bring the pH to 3. The reaction was then neutralized with saturated sodium bicarbonate. The oraganics were then washed 3×50 mL with brine, dried over magnesium sulfate anhydrous, removed under reduced pressure. The pale oil was run through a plug of silica (15 g) to afford the alcohol 5.15 g, 0.026 mol (64%). $C_9H_{14}N_2O_3$.

$^1$H NMR (CDCl$_3$, δ ppm) 1.18–2.15(m, 8H), 3.59(m, 2H), 4.39(m, 1H).

$^{13}$C NMR (CDCl$_3$, δ ppm) 24.45, 25.71, 26.47, 32.56, 34.67, 51.16, 58.85, 160.66, 160.89.

EXAMPLE 5b

To a solution of Example 5a (5.15 g, 0.026 mol) in methylene chloride (100 mL) at 0° C. in an ice bath was added carbon tetrabromide(10.78 g, 0.033 mol). The solution was cooled to 0° C. in an ice bath. Then triphenylphosphine (10.23 g, 0.39 mol) was added portion wise as not to allow the temperature raise above 3° C. The reaction was stirred for 2 hours and the solvent was removed in vacuo. The crude was purified by flash chromatography to yield the bromide (5.9 g, 0.023 mol) in 87% yield.

Elemental analysis calculated for $C_{10}H_{16}N_2O_3$: C, 41.40; H, 5.02; N, 10.73; Br, 30.60. Found: C, 41.59; H, 5.07; N, 10.60, Br, 30.86.

¹H NMR (CDCl₃, δ ppm) 1.50–2.60 (m, 9H), 2.99 (dd, 1H), 3.35 (m, 2H), 4.41 (m, 1H).

¹³C NMR (CDCl₃, δ ppm) 23.89, 25.33, 26.04, 28.06, 31.59, 35.05, 52.79, 159.3, 160.2.

EXAMPLE 5c

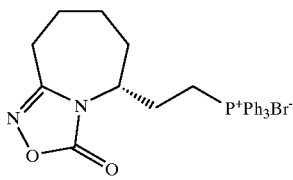

To a solution of Example 5b (5.71 g, 0.026 mol) in toluene (25 mL) was added triphenyl phosphine (7.17 g, 0.027 mol). The reaction refluxed in an oil bath for 16 hours. After cooling, the toluene was decanted from the glassy solid. The solid was triturated with diethyl ether overnight to afford the phosphonium bromide (10.21 g, 0.020 mol) in 90% yield.

¹H NMR (CDCl₃, δ ppm): 1.50–2.9 (m, 11H), 3.58 (m, 1H), 4.16 (m, 1H), 4.41 (m, 1H), 7.6–8.0 (m, 15H).

¹³C NMR (CDCl₃, δ ppm): 24.43, 24.97, 25.50, 55.08, 55.27, 116.9, 118.1, 130.4, 130.6, 133.5, 135.1, 135.2, 159.4, 160.

³¹P NMR (CDCl₃, δ ppm) 26.0.

EXAMPLE 5d

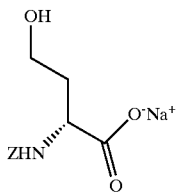

To a 1 L Round Bottom Flask was added N-benzyloxycarbonyl-D-homoserine lactone (97 g, 0.442 mol) in ethanol (500 mL). To the reaction was added solution of sodium hydroxide (1M, 50 mL). The reaction was monitored by thin layer chromatography for 12 hours until the starting material had been consumed. Toluene (60 mL) was added and then solvent was removed in vacuo. The residue was carried on with no further purification.

EXAMPLE 5e

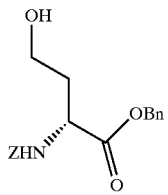

The residue from Example 5d was suspended in DMF in a 1 L Round Bottom Flask. To the suspension was added benzyl bromide (76.9 g, 0.45 mol, 53.5 mL) and the mixture was stirred for 1 hour. A sample was quenched and analyzed by mass spec to indicate the consumption of the starting material and that there was no lactone reformation. To the reaction was added 1 L of ethyl acetate and 500 mL of brine. The aqueous layer was washed 2 additional times with 500 mL of ethyl acetate. The organics were combined, dried over MgSO₄ and concentrated. Silica gel chromatography provided N-benzyloxycarbonyl-S-homoserine benzyl ester as a white solid (80 g).

EXAMPLE 5f

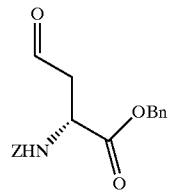

To a 2 L Round Bottom Flask was added pyridinium chlorochromate (187 g, 0.867 mol) and silica gel (197 g) suspended in CH₂Cl₂ (600 mL). To the slurry was added a solution of the product of Example 5e (80 g, 0.233 mol) in CH₂Cl₂ (600 mL). The mixture was stirred for 4 hours. Thin layer chromatography indicated that the starting material was consumed. To the reaction was added 1 L of diethyl ether. The solution was then filtered through a pad of ceilite followed by a pad of silica gel. The solvent was removed in vacuo and the resulting oil was purified by silica gel chromatography to afford the aldehyde (58.8 g) in 38% overall yield.

MH⁺342.5, MH+NH₄⁺359.5.

¹H NMR (CDCl₃, δ ppm) 3.15 (q, 2H), 4.12 (m, 1H), 5.15 (s, 2H), 5.20 (s, 2H), 7.31 (m, 10H), 9.72 (s,1H).

EXAMPLE 5g

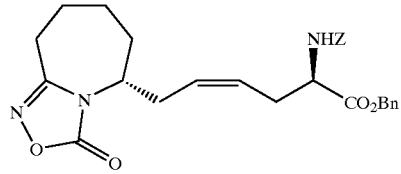

To a 3 L 3-neck flask was added the phosphonium salt from Example 5c (56.86 g, 0.11 mol) that had been dried over P₂O₅ under a vacuum in THF (1 L). The slurry was cooled to −78° C. in a dry-ice bath. To the cold slurry was added KHMDS (220 mL, 0.22 mol) dropwise so that the temperature did not rise above −72° C. The reaction was stirred at −78° C. for 20 minutes and then −45° C. for 2 hours. The temperature was then dropped back to −78° C. and the aldehyde (15.9 g, 0.047 mol) from Example 5f was added in THF (50 mL) dropwise over 45 minutes. The reaction was stirred at −77° C. for 30 minutes then warmed to −50° C. for 1 hour before it was warmed to room temperature over 4 hours. To the reaction was added ethyl acetate (200 mL) and saturated ammonium chloride. The organics were collected, dried over MgSO₄ and concentrated in vacuo. The crude oil was purified on silica chromatography to afford the olefin compound (45.1 g) in 81% yield as a pale yellow viscous oil.

¹H NMR (CDCl₃, δ ppm) 1.4–2.6 (m,.10H), 2.92(d, 1H), 4.17(m, 1H), 4.38(m, 1H), 5.05(q, 2H), 5.40(m, 2H), 7.3(m, 10H).

¹³C NMR (CDCl₃, δ ppm) 29.49, 29.64, 31.32, 39.60, 49.56, 53.98, 61.01, 65.25, 124.14, 127.81, 128.20, 128.55, 128.79, 129.30, 130.96, 135.68, 137.31, 152.59, 157.57, 171.61.

EXAMPLE 5

To a 20 mL vial was added the product from Example 5g (19.77 g, 0.039 mol) in Dioxane (50 mL) and 4N aqueous HCl (250 mL). This solution was added a cat. amount of 10% Pd on carbon in a hydrogenation flask. The flask was pressurized with $H_2$ (50 psi) for five hours. The reaction was monitored by mass spec and the starting material had been consumed. The solution was filtered through a pad of celite and washed with water. The solvent was removed by lyophollization to afford the title compound (7.52 g) in 81% yield.

$MH^+$242.2, $MH+NH_4^+$259.2.

$^1$H NMR (CD$_3$ODδ ppm) 1.2–2.0 (m, 15H), 2.42 (d, 1H), 2.65 (dd, 1H), 3.49 (m, 1H), 3.98 (t, 1H), 7.26 (s), 8.05 (s), 8.35 (s).

$^{13}$C NMR (CDCl$_3$, δ ppm) 24.43, 25.58, 26.00, 26.10, 32.75, 33.45, 35.31, 53.76, 54.55, 157.27, 175.13.

EXAMPLE 6

(αS,2S)-α-aminohexahydro-7-imino-1H-azepine-2-hexanoic acid, trihydrate hydrochloride

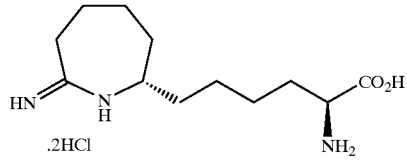

EXAMPLE 6a

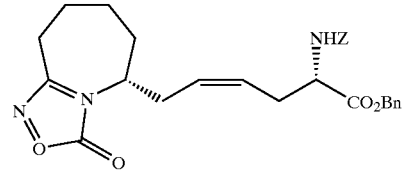

To a 1 L 3-neck flask was added the phosphonium salt from Example 5c (21.21 g, 0.041 mol) in THF (200 mL). The slurry was cooled to −78° C. in a dry-ice bath. To the cold slurry was added KHMDS (88 mL, 0.044 mol) dropwise so that the internal temperature did not rise above −72° C. The reaction stirred at −78° C. for 20 minutes then −45° C. for 1 hour. The temperature was then dropped back to −78° C. and the aldehyde (15.9 g, 0.047 mol) (prepared as in Example 5(d–f) using N-benzyloxycarbonyl-L-homoserine lactone) was added in THF (50 mL) dropwise over 45 minutes. The reaction was stirred at −77° C. for 30 minutes then warmed to −50° C. for 30 minutes then warmed to room temperature over 4 hours. To the reaction was added ethyl acetate (100 mL) and saturated ammonium chloride. The organics were collected, dried over MgSO$_4$ and concentrated in vacuo. The crude oil was purified on silica chromatography to afford the olefin compound (9.0 g) in 45% yield as a pale yellow viscous oil.

$^1$H NMR (CDCl$_3$, δ ppm) 1.4–2.6 (m, 10H), 2.92 (d, 1H), 4.17 (m, 1H), 4.38 (m, 1H), 5.05 (q, 2H), 5.40 (m, 2H), 7.3 (m,10H).

$^{13}$C NMR (CDCl$_3$, δ ppm) 29.49, 29.64, 31.32, 39.60, 49.56, 53.98, 61.01, 65.25, 124.14, 127.81, 128.20, 128.55, 128.79, 129.30, 130.96, 135.68, 137.31, 152.59, 157.57, 171.71.

EXAMPLE 6

To a 20 mL vial was added the product from Example 6a in dioxane (5 mL) and 4N aqueous HCl (16 mL). This solution was added a cat. amount of 10% Pd on carbon in a hydrogenation flask. The flask was pressurized with $H_2$ (50 psi) for five hours. The reaction was monitored by mass spec and the starting material had been consumed. The solution was filtered through a pad of ceilite and washed with water. The solvent was removed by lyophilization to afford the title compound (98.7 mg) in 79.4% yield.

$MH^+$242.2, $MH+NH4^+$259.2.

$^1$H NMR (CD$_3$OD, δ ppm) 1.2–2.0 (m, 15H), 2.42 (d, 1H), 2.6 (dd, 1H), 3.49 (m, 1H), 3.98 (t, 1H).

$^{13}$C NMR (CDCl$_3$, δ ppm) 24.43, 25.58, 26.00, 26.10, 32.75, 33.45, 35.31, 53.76, 54.55, 157.27, 175.13.

EXAMPLE 7

(2S,4Z)-2-amino-6-[(2R)-hexahydro-7-imino-1H-azepin-2-yl]-4-hexenoic acid

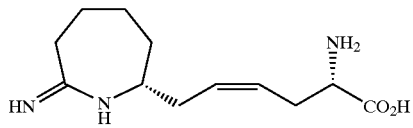

EXAMPLE 7a (2S,4Z)-6-[(2R)-hexahydro-7-imino-1H-azepin-2-yl]-2-[[(phenylmethoxy)carbonyl]amino]-4-hexenoic acid, phenylmethyl ester

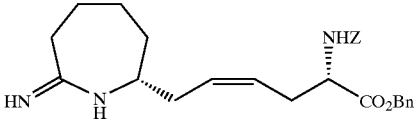

To a 50 mL flask was added a sample of Example 6a (1.5 g, 2.97 mmol) in methanol (25 mL). A 60% solution of glacial acetic acid (16 mL) was then added to the reaction mixture. A precipitate was observed. Additional methanol was added to dissolve the solid (1 mL). To the reaction was then added zinc dust (0.200 g). The reaction was sonicated for 4 hours during which the temperature was maintained at 37° C. The reaction was monitored by TLC and MS until the starting material was consumed and a mass corresponding to the product was observed. The solution was decanted from the zinc and a 30% solution of acetonitrile/water (100 mL) was added to the filtrate. The reaction was purified with 52% acetonitrile/water in two runs on the Waters Preparatory HPLC [a gradient of from 20% to 70% acetonitrile over 30 minutes]. Lyophilization of the resulting product afforded the title material of Example 7a (1.01 g) in 73% yield as a white solid.

$MH^+$464.4, $MH+Na^+$486.4.

$^1$H NMR (CD$_3$OD, δ ppm): 1.2–2.0 (m, 8H), 2.42 (m, 2H), 2.6 (m, 5H), 3.49 (q, 1H), 4.31 (t, 1H), 5.15 (s, 2H), 5.22 (s, 2H), 5.43 (q, 1H), 5.59(q, 1H), 7.25 (bs, 10H).

$^{13}$C NMR (CDCl$_3$, δ ppm): 24.37, 29.61, 30.76, 32.45, 33.73, 34.42, 55.40, 57.09, 68.06, 68.07, 122.3, 124.9, 128.76, 129.09, 129.28, 129.39, 129.51, 129.61, 155.71, 158.35, 173.90.

EXAMPLE 7

To a 250 mL flask was added the product of Example 7a (1.0 g, 2.2 mmol) in 4 M HCl (100 mL). The reaction was refluxed overnight, monitored by MS until the starting material had been consumed and the mass for the product was observed. The reaction, without further work up was purified in two runs on the Water's prep reverse phase column using 18% acetonitrile/water [0% to 30% acetonitrile/water over 30 minutes]. Lyophilization of the combined fractions afforded the title product (0.34 g) in 64% yield as a cream colored foam.

MH$^+$240.3, MH+Na$^+$486.4.

$^1$H NMR (CD$_3$OD, δ ppm): 1.2–2.0 (m, 6H), 2.35 (m, 2H), 2.45 (dd, 2H), 2.69 (m, 2H), 3.61 (dt, 1H), 3.98 (t, 1H), 5.59(m, 1H), 5.65 (m, 1H).

$^{13}$C NMR (CDCl$_3$, δ ppm): 23.65, 24.66, 32.51, 32.84, 33.1, 33.25, 54.10, 56.1, 126.80, 129.33, 153.33, 172.52.

EXAMPLE 8

(2S,4E)-2-amino-6-[(2R)-hexahydro-7-imino-1H-azepin-2-yl]-4-hexenoic acid

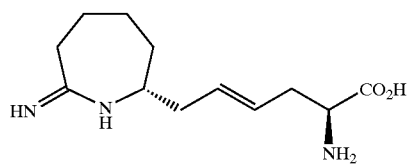

EXAMPLE 8a (2S,4E)-2-[[(phenylmethoxy)carbonyl]amino]-6-[(5R)-6,7,8,9-tetrahydro-3-oxo-3H,5H-[1,2,4]oxadiazolo[4,3-α]azepin-5-yl]-4-hexenoic acid, phenylmethyl ester

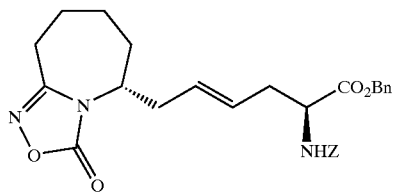

To a 250 mL flask was added Example 6a (2.0 g, 3.9 mmol) and phenyl disulfide (0.860 g, 3.9 mmol) in a cyclohexane (70 mL)/benzene(40 mL) solution. Nitrogen was bubbled through the solution to purge the system of oxygen. The reaction was exposed to a short wave UV lamp for the weekend. The reaction was evaluated by normal phase HPLC (ethyl acetate/hexane). 71% of the trans isomer and 29% of the cis isomer was observed. The reaction was subjected to an additional 3 days of UV upon which 84% of the starting material converted to the trans isomer and 16% of the starting cis isomer remained. Purification by chromatography afforded Example 8a (0.956 g) in 48% yield.

MH$^+$506.1, MH+NH4$^+$523.2.

$^1$H NMR (CD$_3$OD, δ ppm): 1.2–2.0 (m, 8H), 2.42–2.6 (m, 6H), 2.91 (dd, 1H), 4.19 (m, 1H), 4.31 (dt, 1H), 5.09 (s, 2H), 5.11 (s, 2H), 5.18 (dt, 1H), 5.27(m, 1H), 7.25 (bs, 10H).

EXAMPLE 8b (2S,4E)-6-[(2R)-hexahydro-7-imino-1H-azepin-2-yl]-2-[[(phenylmethoxy)carbonyl]amino]-4-hexenoic acid, phenylmethyl ester, monohydrochloride

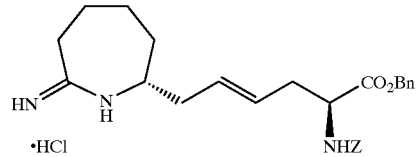

A sample of the product of Example 8a (0.956 g, 1.9 mmol) in MeOH (80 mL) was deprotected by method of Example 7a with Zn dust (1.5 g) and 60% HOAc/H$_2$O (40 mL). The resulting product was purified by reverse phase chromatography to afford the title material (0.248 g) in 28% yield.

EXAMPLE 8

The product of Example 8b (0.248 g, 0.53 mmol) was transformed into the title product by the method of Example 7 using HCl (2 mL), H$_2$O (2 mL), CH$_3$CN (4 mL). The crude product was purified by reverse phase chromatography to afford the title product of Example 8 (0.073 g) in 57% yield.

MH$^+$240.3, MH+Na$^+$486.4.

$^1$H NMR (CD$_3$OD, δ ppm) 1.2–2.0 (m, 6H), 2.35 (t, 2H), 2.55–2.82 (m, 4H), 3.68 (dt, 1H), 4.05 (t, 1H), 5.65 (m, 2H).

EXAMPLE 9

(2S,4Z)-2-amino-6-[(5R)-6,7,8,9-tetrahydro-3-oxo-3H,5H-[1,2,4]oxadiazolo[4,3-α]azepin-5-yl]-4-hexenoic acid, monohydrochloride

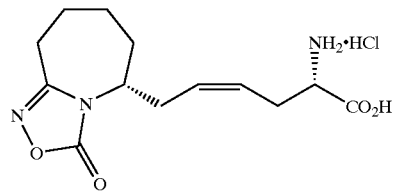

A sample of the product of Example 6a is converted to the title compound by reaction with HCl following the method of Example 8.

EXAMPLE 10

(2S,4E)-2-amino-6-[(5R)-6,7,8,9-tetrahydro-3-oxo-3H,5H-[1,2,4]oxadiazolo[4,3α]alazepin-5-yl]-4-hexenoic acid, monohydrochloride

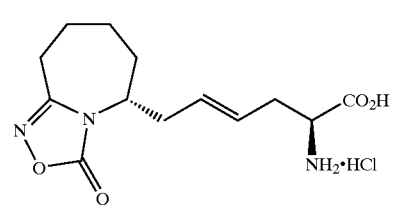

A sample of the product of Example 8a is converted to the title compound by reaction with HCl following the method of Example 8.

EXAMPLE 11

(2S,4Z)-2-amino-6-[(2R,7Z)-hexahydro-7-(hydroxyimino)-1H-azepin-2-yl]-4-hexenoic acid, monohydrochloride

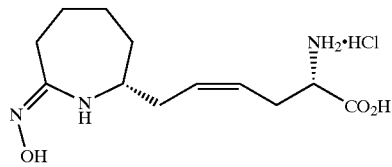

A sample of the product of Example 9 is converted to the title compound by reaction with aqueous potassium or sodium hydroxide.

EXAMPLE 12

(2S,4E)-2-amino-6-[(2R,7Z)-hexahydro-7-(hydroxyimino)-1H-azepin-2-yl]-4-hexenoic acid, monohydrochloride

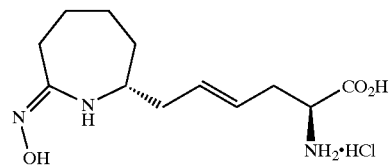

A sample of the product of Example 10 is converted to the title compound by reaction with aqueous potassium or sodium hydroxide.

Particular novel intermediate compounds useful in the synthesis of compounds of the present invention are all the enantiomers, stereoisomers and geometric isomers of the following:

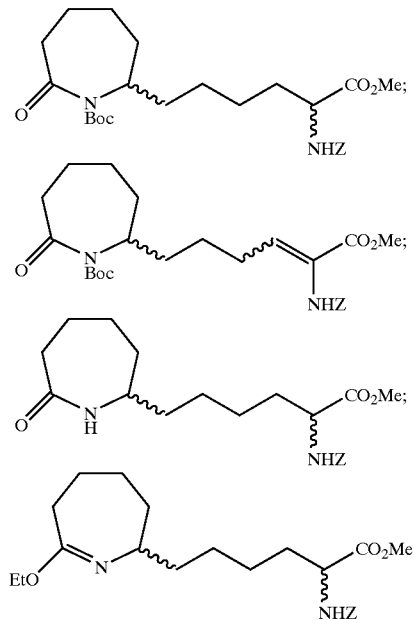

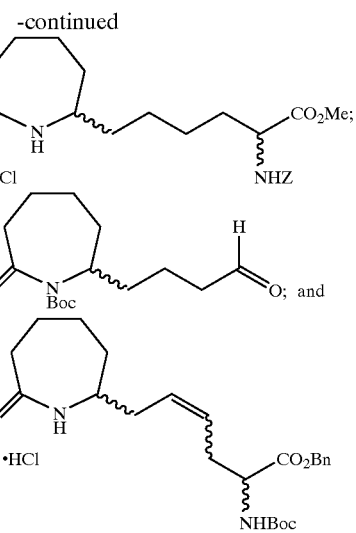

Biological Activity

The activity of the above listed compounds can be determined in the following assays:

Citrulline Assay for Nitric Oxide Synthase

Nitric oxide synthase (NOS) activity is measured by monitoring the conversion of [$^3$H]-arginine to [$^3$H]-citrulline (Bredt and Snyder, *Proc. Natl. Acad. Sci. U.S.A.*, 87, 682–685, 1990 and Misko et al, *Eur. J. Pharm.*, 233, 119–125, 1993). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a lambda cDNA library made from RNA extracted from a colon sample from a patient with ulcerative colitis. The cDNA for human endothelial constitutive NOS (hecNOS) is isolated from a lambda cDNA library made from RNA extracted from human umbilical vein endothelial cells (HUVEC) and the cDNA for human neuronal constitutive NOS (hncNOS) is isolated from a lambda cDNA library made from RNA extracted from human cerebellum obtained from a cadaver. The recombinant enzymes are expressed in Sf9 insect cells using a baculovirus vector (Rodi et al, in *The Biology of Nitric Oxide, Pt. 4: Enzymology Biochemistry and Immunology*; Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 µL of enzyme is added to 40 µL of 50 mM Tris (pH 7.6) in the presence or absence of test compounds and the reaction initiated by the addition of 50 µL of a reaction mixture containing 5 mM Tris (pH 7.6), 2.0 mg/mL bovine serum albumin, 2.0 mM DTT, 4.0 mM CaCl$_2$, 20 µM FAD, 100 PM tetrahydrobiopterin, 0.4–2.0 mM NADPH and 60 µM L-arginine containing 0.9 µCi of L-[2,3-$^3$H]-arginine. The final concentration of L-arginine in the assay is 30 µM. For hecNOS or hncNOS, calmodulin is included at a final concentration of 40–100 nM. Following incubation at 37° C. for 15 minutes, the reaction is terminated by addition of 300 µL of cold stop buffer containing 10 mM EGTA, 100 mM HEPES, pH 5.5 and 1 mM citrulline. [3H]-Citrulline is separated by chromatography on Dowex 50W X-8 cation exchange resin and radioactivity determined with a liquid scintillation counter. Results are reported in Table I as the IC$_{50}$ values of compounds for hiNOS, hecNOS and hncNOS.

TABLE I

| Example Number | IC$_{50}$ [μM] | | |
|---|---|---|---|
| | hiNOS | hecNOS | hncNOS |
| 1 | <3 | >30 | >3 |
| 2 | <5 | >150 | >10 |
| 4 | <3 | >15 | >3 |

In Vivo Assay

Rats are treated with an intraperitoneal injection of 10–12.5 mg/kg of endotoxin (LPS) to induce systemic expression of inducible nitric oxide synthase, resulting in markedly elevated plasma nitrite/nitrate levels. Compounds are administered orally 0.5–1 hours prior to LPS administration and plasma nitrite/nitrate levels are determined 5 hours following LPS administration. Example 1 ((2S,5E)-2-amino-6-fluoro-7-[(1-iminoethyl)amino]-5-heptenoic acid, dihydrochloride) inhibited the LPS-induced increase in plasma nitrite/nitrate levels in a dose dependent manner, demonstrating the ability to inhibit inducible nitric oxide synthase activity in vivo, with an observed ED$_{50}$ value of <3 mg/kg (Table II).

TABLE II

ED$_{50}$'s for Examples determined in endotoxin-treated rats
All compounds administered orally unless otherwise noted.

| Example No. | ED$_{50}$ (mg/kg) |
|---|---|
| 1 | <3 |
| 4 | <5 |

Raw Cell Nitrite Assay

RAW 264.7 cells can be plated to confluency on a 96-well tissue culture plate grown overnight (17 h) in the presence of LPS to induce NOS. A row of 3–6 wells can be left untreated and served as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 mL of buffer containing L-arginine (30 mM) +/− inhibitors for 1 h. The assay can be initiated by warming the plate to 37° C. in a water bath for 1 h. Production of nitrite by intracellular iNOS will be linear with time. To termninate the cellular assay, the plate of cells can be placed on ice and the nitrite-containing buffer removed and analyzed for nitrite using a previously published fluorescent determination for nitrite. T. P. Misko et al, *Analytical Biochemistry*, 214, 11–16 (1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 25–45 mg in weight and one or two explants per well are placed into 48 well culture plates with 500 μL of culture media per well. The culture media was either a custom modification of Minimum Essential Medium (Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 μM L-Arginine (Sigma), 2 mM L-glutamine, 1×HL-1 supplement (BioWhittaker), 50 mg/ml ascorbic acid (Sigma) and 150 pg/ml recombinant human IL-1β (RD Systems) to induce nitric oxide synthase. Compounds are then added in 10 μL aliquots and the explants incubated at 37° C. with 5% CO$_2$ for 18–24 hours. The day old supernatant is then discarded and replaced with fresh culture media containing recombinant human IL-1β and compound and incubated for another 20–24 hours. This supernatant is analyzed for nitrite with a fluorometric assay (Misko et al, *Anal. Biochem.*, 214, 11–16, 1993). All samples are done in quadruplicate. The explants are weighed and the nitrite levels normalized to weight. Unstimulated controls are cultured in media in the absence of recombinant human IL-1β. IC$_{50}$ values (Table III) are determined from plotting the percent inhibition of nitrite production at six different concentrations of inhibitor.

TABLE III

| Example No. | IC$_{50}$ [μM] |
|---|---|
| 1 | <10 |
| 4 | <10 |

Assay for Time Dependent Inhibition

Compounds are evaluated for time dependent inhibition of human NOS isoforms by preincubation of the compound with the enzyme at 37° C. in the presence of the citrulline enzyme assay components, minus L-arginine, for times ranging from 0–60 minutes. Aliquots (10 μL) are removed at 0, 10, 21 and 60 minutes and immediately added to a citrulline assay enzyme reaction mixture containing L-[2,3-$^3$H]-arginine and a final L-arginine concentration of 30 μM in a final volume of 100 μL. The reaction is allowed to proceed for 15 minutes at 37° C. and terminated by addition of stop buffer and chromatography with Dowex 50W X-8 cation exchange ion exchange resin as described for the citrulline NOS assay. The % inhibition of NOS activity by an inhibitor was taken as the per cent inhibition in activity compared to control enzyme preincubated for the same time in the absence of inhibitor. Data shown in Table IV is the % inhibition after 21 and 60 minutes preincubation of inhibitor with enzyme.

TABLE IV

| Example No. | hiNOS | hecNOS | hncNOS |
|---|---|---|---|
| 1 | 75% @ 2.8 μM @ 21 min | 11% @ 33 μM @ 21 min | 0% @ 5 μM @ 21 min |
| | 76% @ 2.8 μM @ 60 min | 11% @ 33 μM @ 60 min | 0% @ 5 μM @ 60 min |
| 2 | 34% @ 4.2 μM @ 21 min | 9% @ 173 μM @ 21 min | 0% @ 13 μM @ 21 min |
| | 38% @ 4.2 μM @ 60 min | 0% @ 173 μM @ 60 min | 0% @ 13 μM @ 60 min |
| 4 | 86% @ 2.2 μM @ 21 min | 18% @ 15 μM @ 21 min | 0% @ 3 μM @ 21 min |
| | 85% @ 2.2 μM @ 60 min | 16% @ 15 μM @ 60 min | 0% @ 3 μM @ 60 min |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula:

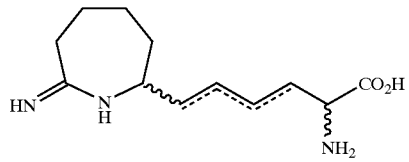

or a pharmaceutically acceptable salt thereof.

2. The compound of claim 1 wherein the compound is represented by the formula:

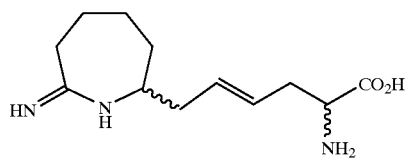

or a pharmaceutically acceptable salt thereof.

3. The compound of claim 2 wherein the compound is represented by the formula:

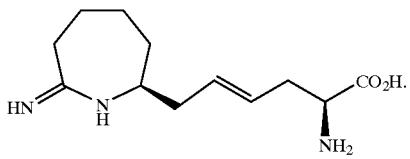

4. The compound of claim 2 wherein the compound is represented by the formula:

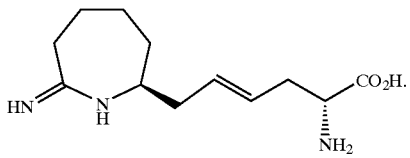

5. The compound of claim 2 wherein the compound is represented by the formula:

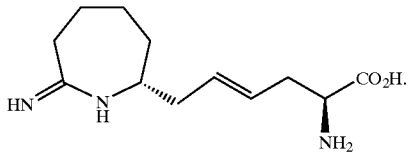

6. The compound of claim 2 wherein the compound is represented by the formula:

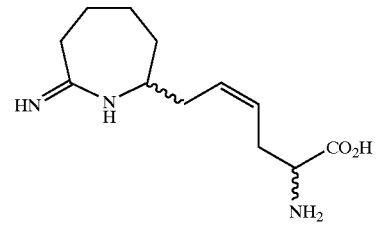

7. A compound of the formula:

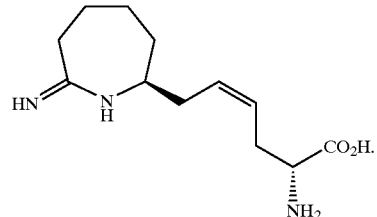

or a pharmaceutically acceptable salt thereof.

8. The compound of claim 7 wherein the compound is represented by the formula:

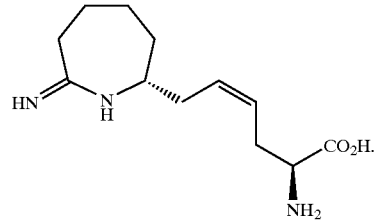

9. The compound of claim 7 wherein the compound is represented by the formula:

10. The compound of claim 7 wherein the compound is represented by the formula:

11. The compound of claim 7 wherein the compound is represented by the formula:

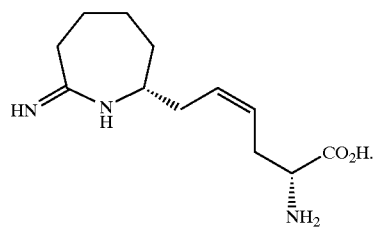

12. A compound of the formula:

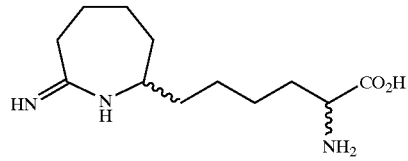

or a pharmaceutically acceptable salt thereof.

13. The compound of claim 12 wherein the compound is represented by the formula:

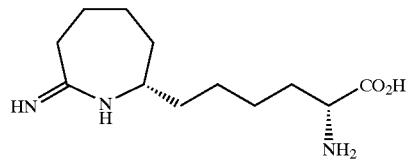

or a pharmaceutically acceptable salt thereof.

14. The compound of claim 12 wherein the compound is represented by the formula:

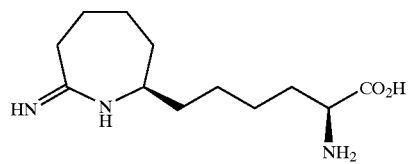

or a pharmaceutically acceptable salt thereof.

15. The compound of claim 12 wherein the compound is represented by the formula:

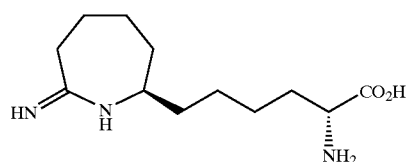

or a pharmaceutically acceptable salt thereof.

16. The compound of claim 12 wherein the compound is represented by the formula:

or a pharmaceutically acceptable salt thereof.

17. A pharmaceutical composition comprising a compound of claim 12 and a pharmaceutically acceptable carrier.

18. A compound or salt selected from the group consisting of:

wherein Z is benzyloxycarbonyl, Boc is tert-butoxycabonyl, and Bn is benzyl.

19. The compound of claim 18 wherein said compound is

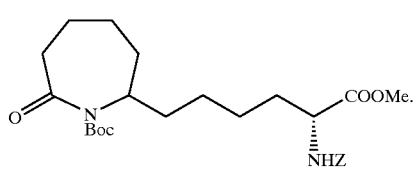

20. The compound of claim 18 wherein said compound is

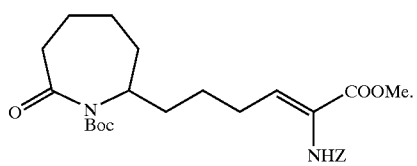

21. The compound of claim 18 wherein said compound is

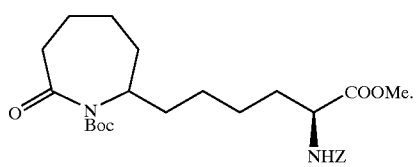

22. The compound of claim 18 wherein said compound is

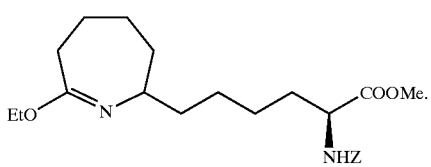

23. The salt of claim 18 wherein said salt is

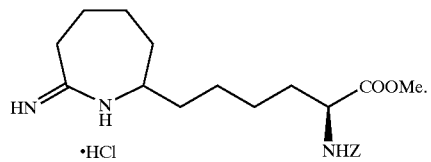

24. The compound of claim 18 wherein said compound is

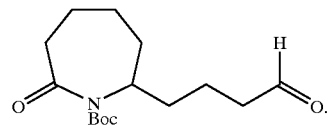

25. The salt of claim 18 wherein said salt is

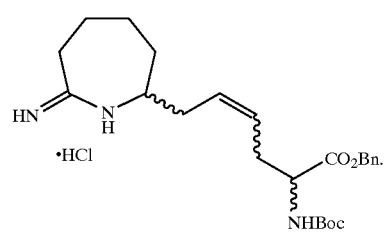

26. A compound of the formula:

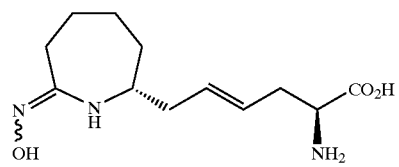

or a pharmaceutically acceptable salt thereof.

27. A compound of the formula:

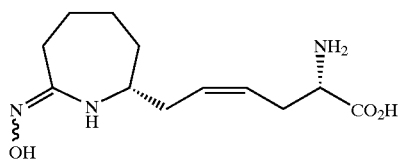

or a pharmaceutically acceptable salt thereof.

* * * * *